(12) United States Patent
Whitbourne

(10) Patent No.: US 8,609,642 B2
(45) Date of Patent: Dec. 17, 2013

(54) SKIN TREATMENT COMPOSITIONS

(75) Inventor: Richard James Whitbourne, Niagara Falls, NY (US)

(73) Assignee: Ex-Tek, LLC, Markham, Ontario, CA (US)

( * ) Notice: Subject to any disclaimer, the term of this patent is extended or adjusted under 35 U.S.C. 154(b) by 0 days.

(21) Appl. No.: 13/261,062

(22) PCT Filed: Jun. 3, 2010

(86) PCT No.: PCT/US2010/037245
§ 371 (c)(1),
(2), (4) Date: Dec. 5, 2011

(87) PCT Pub. No.: WO2010/141711
PCT Pub. Date: Dec. 9, 2010

(65) Prior Publication Data
US 2012/0077784 A1    Mar. 29, 2012

Related U.S. Application Data

(60) Provisional application No. 61/183,834, filed on Jun. 3, 2009, provisional application No. 61/257,205, filed on Nov. 2, 2009.

(51) Int. Cl.
*A61K 31/60* (2006.01)
*A61K 31/192* (2006.01)
*A61K 31/198* (2006.01)
*A61K 31/19* (2006.01)
*A61K 31/20* (2006.01)
*A61K 31/045* (2006.01)

(52) U.S. Cl.
USPC ........... 514/159; 514/557; 514/560; 514/574; 514/561; 514/568; 514/563; 514/724; 514/730

(58) Field of Classification Search
None
See application file for complete search history.

(56) References Cited

U.S. PATENT DOCUMENTS

| 6,579,543 B1 | 6/2003 | McClung |
| 2005/0035327 A1 | 2/2005 | Canada et al. |
| 2005/0163737 A1 | 7/2005 | Lemoine et al. |
| 2006/0052452 A1* | 3/2006 | Scholz ........................ 514/557 |
| 2007/0027119 A1* | 2/2007 | Ahmed et al. ................ 514/159 |
| 2008/0287538 A1 | 11/2008 | Scholz et al. |

FOREIGN PATENT DOCUMENTS

| EP | 0970691 A1 | 1/2000 |
| EP | 1374903 A1 | 1/2004 |
| JP | 2008-110993 A | 5/2008 |
| WO | WO-92/10992 A1 | 7/1992 |
| WO | WO-98/35651 A1 | 8/1998 |
| WO | WO-99/30677 A1 | 6/1999 |
| WO | WO-2004/069220 A1 | 8/2004 |
| WO | WO-2006/053007 A2 | 5/2006 |
| WO | WO-2007/092085 A2 | 8/2007 |

OTHER PUBLICATIONS

Faoagali, Primary Intention pp. 156-160 published Nov. 1999.*
Ramelet et al. Management of Leg Ulcers; 1999, pp. 20-23.*
British Medical Journal ("BMJ") p. 1232 published May 13, 1978.*
Bryce et al. J. Soc. Cosmet. Chem. 1978, 29, 3-24.*
Chantelau et al., "Acute cutaneous complications and catheter needle colonization during insulin-pump treatment", Jul. 1, 1987 http://www.ncbi.nlm.nih.gov/pubmed/3622204.
International Search Report (PCT/ISA/210) issued in PCT application No. PCT/US2010/037245, dated Jul. 30, 2010.
Written Opinion issued in PCT application No. PCT/US2010/037245, dated Jul. 30, 2010.
Chantelau et al., "Acute cutaneous complications and catheter needle colonization during insulin-pump treatment", Diabetes Care, vol. 10, No. 4, pp. 478-482, 1987.
European Supplementary Search Report dated Dec. 10, 2012, issued in European Patent Application No. 10784088.6.

* cited by examiner

*Primary Examiner* — Jeffrey S. Lundgren
*Assistant Examiner* — Michael Schmitt
(74) *Attorney, Agent, or Firm* — Venable LLP; Nancy J. Axelrod; Michael A. Gollin

(57) ABSTRACT

The present invention relates to compositions, kits and methods for treating skin at sites of concerns such as infectious lesions and/or points of insertion of an insertable medical device to prevent contamination such as infections or protein absorption that may interfere with the function of the device. The composition can be a topical skin treatment composition that includes polyethylene glycol (PEG), triclosan, one or more of a salicylate, bronopol, and an acrylic emulsion, and, optionally, a solvent.

16 Claims, No Drawings

SKIN TREATMENT COMPOSITIONS

This application is a National Stage Application of International Application No. PCT/US2010/037245, filed Jun. 3, 2010, which claims priority to U.S. Provisional application 61/183,834, filed Jun. 3, 2009 and U.S. Provisional application 61/257,205 filed Nov. 2, 2009, all of which are incorporated by reference herein in their entirety.

FIELD OF THE INVENTION

The invention relates to compositions, methods and kits for skin treatment. More particularly, the invention relates to compositions, methods and kits for treatment of a skin condition or pre-treatment of a point of insertion of a medical device.

BACKGROUND OF THE INVENTION

Diabetes is a chronic disease that can be managed, but is not ordinarily cured by therapies and lifestyle changes. Patients typically experience a higher risk of disorders, such as atherosclerosis, peripheral artery disease, kidney disease, blindness, neuropathy, infections, and other disorders than non-diabetic patients especially at the extremities. This is especially the case for patients unable or unwilling to maintain their blood glucose levels at or close to normal ranges. Patients who control their blood glucose within or near the normal ranges by combinations of diet, appropriate medication, and exercise are found to experience reduced risk of many of the disorders that are associated with diabetes.

Foot infections are a particular disorder known to occur in diabetic patients, and tens of thousands of diabetic patients are subjected to toe and foot amputation annually because of foot infections, i.e., Diabetic Foot Ulcers (DFU's).

A newer therapy for type 1 and type 2 insulin dependent diabetics includes the use of insulin pumps and continuous glucose sensors. Insulin pumps use an infusion set having a needle that is percutaneously inserted into soft tissue. A portion of the needle remains outside of the insertion site, thus providing a pathway for skin flora to migrate along the inserted needle beneath the skin and proliferate, leading to infections around the inserted needle. Continuous glucose sensors are also inserted percutaneously into soft tissue, and provide readings of interstitial glucose levels. These devices can also lead to infections by the same circumstances described above for insulin pump needles.

In the course of placing an insertable or implantable device in a patient, contamination can occur, including infections and protein absorption at and around the inserted portion of the devices. Such contamination can occur rapidly, within a few days, and often interferes with the function of the device. Some devices may be coated to prevent such contamination. However, even with coated devices, exudate can seep from the insertion site and wet skin flora which can then diffuse back into the patient along the wetted device surface, thereby causing infection. The insertion site will also become wetted as a result of activities such as showers, and such wetting of the site may also lead to infections. Typically, when a needle or catheter is inserted, the area of insertion is cleaned with an antiseptic. However, such treatment is temporary, and the site may be palpated after swabbing, which can contaminate the site.

SUMMARY OF THE INVENTION

The present invention provides anti-infective compositions that are particularly suited and effective in treating a variety of skin conditions. The compositions are applied topically, and the compositions may be delivered transdermally to provide targeted, localized, effective concentrations of agents. Typical side effects of systemic antibiotic administration are reduced because the agents are not administered systemically, and the amounts of agents administered, while small, nevertheless achieve higher and more effective drug concentrations within the treated infectious locations, and extremely low systemic concentrations result. Thus, enhanced therapy is achieved compared with systemic antibiotic administration.

The skin treatment compositions can be for use with insertable medical devices to be inserted into a patient. The present invention also provides topical, anti-infective compositions that are useful in preparing device insertion sites to resist infections around inserted devices, and to permit devices to remain indwelling for longer periods while remaining patent.

The present invention relates to skin treatment compositions including polyethylene glycol (PEG), triclosan, one or more of a salicylate, bronopol, and an acrylic emulsion, and, optionally, a solvent. In some aspects, the salicylate may be present in the composition as salicylic acid, in an amount of about 0.5 to about 1.5% w/w, or acetylsalicylic acid, in an amount of about 0.4 to 0.5% w/w. In other aspects, the composition may have about 0.05 to about 2.0% w/w triclosan or about 0.05 to about 0.5% w/w bronopol. In yet other embodiments, the composition includes about 0.01% to about 8.0% w/w of one or more of triclosan, acetylsalicylic acid, salicylic acid, or bronopol. In some aspects, the composition includes salicylic acid and bronopol.

In some embodiments, the composition may include polyethylene glycol (PEG) present as one or more of PEG 400, PEG 8000 or PEG 35000, present in an amount of, for example, about 0.001% to about 40% w/w. In other aspects, the composition may have the acrylic emulsion Rhoplex B15-J, in an amount of, for example, about 5 to 20% w/w. In yet other aspects, the composition may include a solvent that can be one or more of water, acetonitrile, acetone, methylethylketone, denatured ethanol, ethanol, saline solution, normal saline solution, methylene chloride, carbontetrachloride, tetrahydrofuran, isopropyl alcohol, rum, other alcohols, amines, amides, 1,3-dioxalane, ketones, esters, cyclic compounds, glycols, carboxylic acids, and aromatic solvents. Solvents may be present in an amount of, for example, about 2% to about 99% w/w.

In some embodiments, the invention relates to a method of treating the skin of an individual, wherein the individual has a site of concern on the skin in need of treatment, including applying to the site of concern a topical skin treatment composition having polyethylene glycol, triclosan, and one or more of a salicylate, bronopol, and an acrylic emulsion. In particular aspects, the individual may be suffering from diabetes. In other aspects, the method further includes selecting a site of concern on the skin of the individual. In some embodiments, the site of concern on the skin in need of treatment may be one or more of a lesion, cut, wound, bruise, puncture, breech, infection, ulcers, macule, patch, scale, wrinkle, papule, plaque, nodule, vesicle, bulla, pustule, cyst, erosion, ulcer, fissure, wheal, telangiectasia, burrow, scale, crust, lichenification, excoriation, a punctuate, puncture, abrasion, induration, burn, rash, decubital ulcer, bed sores, pressure sores, atrophy, or other trauma to the skin. In other embodiments, the site of concern on the skin in need of treatment is a lesion, skin ulcer, such as a diabetic foot ulcer, refractory skin infection, or an ulceration or infection in a limb, such as a foot. In some aspects, the composition is applied at least daily or at least twice a day.

In yet other embodiments, the site of concern in need of treatment is an insertion point for a medical device. In other aspects, the method includes inserting the medical device at the site of concern. The method may further include allowing the solvent to evaporate to produce a skin treatment layer/coating on the skin prior to inserting a medical device. In yet other exemplary embodiments, the method can include selecting as the site of concern a point of insertion of a medical device into the tissue of a patient that will create a puncture, and further including providing the insertable medical device, treating the tissue of the patient at the point of insertion by applying the skin treatment composition; and inserting the device into the patient at the point of insertion through the skin treatment composition. In yet other aspects, the composition may be effective to reduce infection at a medical device insertion site and enable insulin or other drug burden to remain in an effective range during an extended period, if the composition is applied prior to insertion. In other aspects, the medical device may be an insulin pump needle or a continuous glucose monitor, or a needle, an infusion set or device, a peripheral venous catheter or needle, an indwelling infusion needle, a butterfly needle, a subcutaneous access device, an insulin pump needle, a patient controlled analgesia (PCA) pump needle, an arterial catheter, a central venous catheter, a dialysis catheter, a peritoneal dialysis catheter, a nephrostomy catheter, a percutaneous cystostomy catheter, an indwelling paracentesis or pleurocentesis catheter or drain, a percutaneous nephrostomy, a cystostomy tube, a spinal or epidural catheter, and a sensor.

DETAILED DESCRIPTION OF THE PREFERRED EMBODIMENTS

The present invention relates to compositions, methods and kits including a topical skin treatment composition having various therapeutic properties for the treatment of skin conditions and to prevent, reduce, or eliminate the incidence and/or severity of maladies associated with skin breeches or other abnormalities due to external and internal sources.

In some embodiments, the present invention relates to a topical skin treatment composition having polyethylene glycol, triclosan, one or more of a salicylate, bronopol, and an acrylic emulsion and, optionally, a solvent.

Due to complications from diabetes, certain materials are discouraged for topical use with diabetics. These include warnings about triclosan, salicylic acid, and bronopol. These are due to skin irritation, redness, burning, and itching. The present compositions and methods avoid such problems.

As used herein, concentrations and weights may be calculated based on "wet" or "liquid" weight, percentages, ratios or amounts, e.g., in the compositions prior to being applied to the skin. These generally may be referred to as pre-application or pre-coating amounts, and include solvent. The term "dry" or "solid" refers to the non-volatile components of the composition which remain after being applied to the skin and after removal of the non-volatile components. Such compositions may be referred to as post-application compositions, coatings or surface layers. The term "about" generally refers to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

The wet composition, formulation or solution may include one or more of triclosan, a salicylate, or bronopol at an individual or a total concentration of from about 0.001 to 50%, 0.001 to 8.0%, 0.5 to 5.5%, 0.01 to 1.4%, 0.1 to 2%, 0.2 to 1.0%, or about 0.2%, 0.3%, 0.4%, 0.5%, 0.6%, 0.7%, 0.8%, 0.9%, 1.0%, 1.5%, 2.0%, 2.5%, 3.0%, 3.5%, 4.0%, 4.5%, 5.0%, or 5.5% by weight (w/w) or a range between any two of these amounts. In some embodiments, the skin treatment dry composition, which is applied to the skin may include about 0.001% to about 8.0% w/w of one or more of triclosan, a salicylate, or bronopol.

Salicylates, as the term is used here, include acetylsalicylic acid and salicylic acid. In some aspects, the composition may include from about 0.5 to about 1.5% w/w salicylic acid. In other aspects, the composition may include salicylic acid in an amount of about 0.57%, 0.87%, 1.12% or 1.28% w/w or a range between any two of these amounts. In yet further aspects, the composition may include from about 0.4 to 0.5% w/w acetylsalicylic acid, or about 0.44% w/w.

Triclosan may also be referred to by its chemical name, 2,4,4'-Trichloro-2'-hydroxy diphenyl ether. In some embodiments, the wet or dry composition may contain from about 0.05 to about 2.0% w/w triclosan. In yet other embodiments, the amount may be from about 0.09 to about 1.5%, or 0.1 to 0.25%, or about 0.09%, 0.10%, 0.11%, 0.14%, 0.25% or 1.4% w/w or a range between any two of these amounts.

Bronopol may also be referred to by its chemical name, 2-bromo-2-nitropropane-1,3-diol. In some embodiments, the wet or dry composition may include bronopol in an amount of from about 0.05 to 0.5%, 0.09 to 0.3%, 0.1 to 0.25%, or about 0.09%, 0.10%, 0.11%, 0.14%, 0.16%, 0.19%, or 0.25% w/w or a range between any two of these amounts.

In other embodiments, the composition may include salicylic acid, triclosan and bronopol.

The polyethylene glycol (PEG) component in the wet or dry composition can be one or more of a variety of different types of PEG, including lower and higher molecular PEG. Polyethylene glycols (PEG) may have molecular weights ranging from about 100 to about 35000. In some aspects, the molecular weight may be from about 3500 to about 35000. Exemplary weights and molecular weight ranges may include about 100, 200, 400, 1200, 1500, 2000, 2500, 3500, 3500-4500, 4000, 4500, 5000, 5500, 6000, 7000-9000, 7000, 8000, 9000, 10000, 11000, 12000, 13000, 15000, 16000-24000, 20000, 30000, or 35000. Available commercial PEG products may be used with the present invention, for example those marketed by SIGMA-ALDRICH, e.g., product numbers P3265 (MW 400), 95904 (MW 3500-4500), 81253 (MW 6000), 81255 (MW 6000), 89510 (MW 7000-9000), 81268 (MW 7000-9000), P2139 (MW 8000), P5413 (MW 8000), P4463 (MW 8000), P5667 (MW 10000), 92897 (MW 8500-11500), 95172 (16000-24000) or 94646 (35000).

The total PEG component may be about 0.001% to 40%, 0.5% to 40%, 5 to 40%, 9 to 37%, or about 9%, 10%, 11%, 12%, 13%, 14%, 15%, 16%, 20%, 25%, 30%, 35%, 37%, 38%, 39% or 40% w/w or a range between any two of these amounts.

In yet other embodiments, the wet composition of the present invention may include a PEG at a concentration from about 0.001% to about 40%, 0.5 to 25%, or from about 5 to 20%, 1 to 10%, 2 to 8%, 3 to 7%, 5 to 6%, 2 to 4%, 4 to 6%, or about 1%, 2%, 3%, 4%, 5%, 6%, 7%, 8%, 9%, 10%, 15%, 20% or 25% w/w or a range between any two of these amounts. In exemplary embodiments, the present invention may have a skin treatment dry composition that is applied to the skin and that includes an amount of PEG from about 50% to 99.9%, or from about 70 to 99%, 73 to 97%, 75 to 95%, 80 to 90%, or about 73%, 80%, 86%, 87%, 89%, 94%, or 97% w/w or a range between any two of these amounts. In some embodiments, the skin treatment composition include about 0.001% to about 40% polyethylene glycol (PEG). In yet other aspects, the polyethylene glycol (PEG) is selected from one or more of PEG 400, PEG 8000 or PEG 35000. The composition may include PEG 400 in an amount of from about 0.5% to 40%, 0.8 to 38%, or about 0.8%, 0.9%, 1.0%, 1.4%, 1.5%, 2%, 3%, 4%, 4.3%, 4.5%, 5%, 10%, 15%, 20%, 25%, 30%, 34%, 35%, 36%, 37%, 38%, 39% or 40% w/w or a range between any two of these amounts. In yet other aspects, the composition may include PEG 8000 in an amount of from about 5 to 10%, or about 6%, 7%, 8%, 9% or 10% w/w or a range between any two of these amounts. In yet further aspects, the composition may include polyethylene glycol (PEG), e.g., PEG 35000 in an amount of from about 10 to 20%, from about 14 to 17%, or about 14%, 15%, 16% or 17% w/w or a range between any two of these amounts.

An acrylic emulsion as used herein may include aqueous acrylic polymer emulsions or a similar emulsion, for example, N'-((4-Carbamimidoyldiazenylphenyl)amino) ethanimidamide, or Rhoplex brand emulsion from Rohm and Haas, including GL 618 (Rohm & Haas), Rhoplex HA-12 (Rohm & Haas), Rhoplex B-959 (Rohm & Haas), Rhoplex B-15 J (Rohm & Haas), Rhoplex NW-1402 (Rohm & Haas), Reynco 124-45 A (Reynolds Company), Reynco 124-45B (Reynolds Company), Reynco 124-16C, and mixtures thereof. In some embodiments, the acrylic emulsion is Rhoplex B15-J.

The acrylic emulsion may be present in a wet or dry composition in an amount of from about 5 to 20%, from about 8 to 15%, or about 8%, 9%, 10%, 11%, 12%, 13%, 14% or 15% w/w or a range between any two of these amounts.

As used herein, the term "solvent" refers to one or more components that is compatible with and dissolves or disperses the ingredients, for example the active ingredients and PEG, to produce a liquid form. In exemplary embodiments, the solvent evaporates from the composition once applied to the skin. The solvent should also be compatible with other agents, polymers and components that may be added to the composition and can be appropriate for human use. In embodiments, the solvent may be selected from solvents that are able to dissolve or disperse the components homogeneously.

Examples of solvents include one or more of the following: water, acetonitrile, acetone, methylethylketone (MEK or 2-Butanone), ethyl alcohol (ethanol), for example, denatured ethanol, saline solution, normal saline solution, methylene chloride, carbon tetrachloride, tetrahydrofuran (THF), isopropyl alcohol (IPA, isopropanol), rum, other alcohols, amines, amides, 1,3-dioxalane, ketones, esters, cyclic compounds, glycols, carboxylic acids and/or aromatic solvents. In other exemplary embodiments, the solvent may be cyclohexanone, toluene, benzyl alcohol, dibutylphthalate, butanol, xylene and/or ethyl benzene.

The solvent may be an aqueous or an organic solvent, or mixtures thereof. The composition may contain solvent in an amount of from about 2 to 99%, 50 to 99%, 50 to 95%, 60 to 91%, 70 to 99%, 70 to 80%, 80 to 90%, or 90 to 98.8%, or about 60%, 63%, 65%, 70%, 75%, 80%, 85% or 90% w/w or a range between any two of these amounts. In some aspects, the composition include water in an amount of from about 40 to 70%, or about 40%, 45%, 47%, 50%, 53%, 55%, 58%, 60%, 61% or 65% w/w or a range between any two of these amounts.

Suitable alcohols include isopropanol (IPA), ethanol (e.g., 190 proof), acetone, rum (e.g., 151 proof) or other topically acceptable alcohols that serve as a solvent for the dry components. In some aspects, the composition may include ethanol in an amount from about 5 to 40%, 7 to 34%, or about 7%, 8%, 9%, 10%, 14%, 15%, 20%, 27%, 30%, 33%, 34%, or 35% w/w or a range between any two of these amounts. In other aspects, the composition may contain 99% isopropyl alcohol (IPA) in an amount of from about 2 to 11%, or about 2%, 2.5%, 2.7%, 3%, 3.5%, 3.7%, 4%, 5%, 6%, 7%, 8%, 9%, 10% or 11% w/w or a range between any two of these amounts. In yet other aspects, the composition may include acetone in an amount of from about 60 to 70% or about 63% or 64% w/w. In further aspects, the composition may contain rum in an amount of from about 30 to 40%, or about 30%, 31%, 32%, 33%, 34% or 35% w/w or a range between any two of these amounts. In other embodiments, the composition may include MEK in an amount of from about 50 to 70%, or 60 to 68%, or about 64%, 65%, 66%, to 67% or a range between any two of these amounts.

In some embodiments, the composition includes salicylic acid, triclosan, bronopol, a low molecular weight polyethylene glycol, for example PEG 400 or a combination of PEG 400 and PEG 8000, water, and alcohol, for example isopropyl alcohol, ethanol, rum or combinations thereof. In other embodiments, the composition may have triclosan, Rhoplex, a high molecular weight polyethylene glycol, for example, PEG 35000, and a solvent, for example, acetone, ethanol, or combinations thereof. In yet other embodiments, the composition contains triclosan, bronopol, Rhoplex, a high molecular weight polyethylene glycol, for example, PEG 35000, and a solvent, for example, ethanol, methylethylketone (MEK), or combinations thereof. The composition may include acetylsalicylic acid, triclosan and bronopol, a low molecular weight polyethylene glycol, for example, PEG 400, PEG 8000 or combinations, and a solvent, for example, water, ethanol, isopropyl alcohol or combinations thereof.

In some embodiments of the invention, the composition may include one or more additional polymers or a polymeric mixture. As used herein the term "polymer" may be a single polymer or a mixture of two or more polymers. In exemplary embodiments, the polymer(s) may be water soluble, water insoluble, water swellable, bioerodable, dispersible, or mixtures of polymers having the same or different properties with respect their resistance to aqueous fluids. The polymer may be bioerodable, bioabsorbable or biostable. In certain aspects, the polymer may provide the composition and coating with a consistency of flexibility and prolonged adherence on the skin and prevent the absorption of proteins at the site of insertion or onto the device surface, thereby resisting or reducing protein encapsulation of area or the device.

As used herein the terms "bioerodable" and "bioabsorbable" materials, e.g., polymer or polymeric compositions, have similar meaning, namely that they are dissolved or otherwise broken down during a period of use on the skin throughout the duration of insertion or implantation of a medical device in a patient. Non-bioabsorbable, insoluble, and biostable materials typically do not dissolve or break down in biological media. The term biocompatible implies that the material does not induce an adverse response when exposed to living tissue other than absorbing proteins and/or other absorbing biological specimens. The term deciduous suggests sloughing off when exposed to body fluids and/or tissue and refers to an appropriate degree of bioerodability and/or bioabsorbability. Bioerodability implies that the material can safely degrade and erode away in living tissue/fluid. Bioerodability can be fairly rapid, as with water-soluble polymers, or can take place over a more extended time period when the process depends on a hydrolysis reaction(s), e.g., as would be the case with polyglycolic acid esters. Effective sloughing off may occur more with more water-soluble polymers, and less with the polymers that dissolve more slowly, e.g., dispersible polymers. On the other hand, some polymers may have surface characteristics that resist protein absorption by mechanisms other than sloughing off of surface molecules in tissue/fluids, and as such are included in this invention. Further, polymers having different breakdown rates in aqueous fluids may be mixed to provide certain properties. When mixtures of a water-soluble polymer and a water-insoluble are prepared, widely differing erosion rates and drug elution rates can be achieved based on the ratios of the different polymers. For example, polymer mixtures that contain a large amount of biostable polymer and a small amount of water-soluble polymer will typically be less hydrophilic and exhibit a slower drug elution rate in aqueous media than polymer mixtures with the reverse polymer composition ratios. Ratios of various polymers can be adjusted to provide a desired elution rate using routine experimentation.

Bioerodable polymers may be water-soluble or dispersible polymers or non-water-soluble polymers that erode via a hydrolytic erosion process. Examples of bioerodable polymers may include polyethylene glycol, polyethylene oxide, polyacrylic acids including salts thereof, or a copolymer thereof, acrylic emulsion copolymer, an acrylate polymer or copolymer, a polymer or copolymer of polylactic acid, a polymer or copolymer of polyglycolic acid, polyacrylamide, polyvinylpyrrolidone, polyurethane, water-soluble cellulose polymer, cellulose acetate phthalate, methylcellulose, polyvinylalcohol and some cellulose esters.

In exemplary embodiments, the polymer may be a copolymer of methylpolyethylene and poly CD,L-lactic acid (Me-PEG-PDLLA 60:40). This copolymer is in the class of poly (alkylene oxide)-poly(ester) block copolymers (e.g., X—Y, X—Y—X, Y—X—Y, R—(Y—X)$_n$, or R—(X—Y)$_n$, where X is a polyalkylene oxide (e.g., poly(ethylene glycol), poly (propylene glycol) and block copolymers of poly(ethylene glycol) and poly(propylene glycol)) (e.g., PLURONIC and PLURONIC R series of polymers from BASF Corporation, Mount Olive, N.J.) and Y is a polyester, where the polyester may include the residues of one or more of the monomers selected from lactide, lactic acid, glycolide, glycolic acid, e-caprolactone, gamma-caprolactone, hydroxyvaleric acid, hydroxybutyric acid, beta-butyrolactone, gamma-butyrolactone, gamma-valerolactone, gamma-decanolactone, delta-decanolactone, trimethylene carbonate, 1,4-dioxane-2-one or 1,5-dioxepan-2one (e.g., PLGA, PLA, PDLLA, PCL, polydioxanone and copolymers thereof) and R is a multifunctional initiator), and where n can be 2 to 12. Compositions that include blends of one or more of these polymers may also be used. In some embodiments, the polymer may be an acrylic emulsion polymer/latex, e.g., RHOPLEX B15-J (~50/50 w/w emulsion in water).

In other embodiments, the composition may include a polymer having functional groups, e.g., carboxyl, amine or hydroxyl groups, which may promote adhesion to skin tissue.

In exemplary embodiments of the invention, the composition may include a non-bioabsorbable or biostable polymer. Examples of non-bioabsorbable or biostable polymers include acrylates, urethanes, polycarbonates, polyamides, polyesters and polyimides, or a biostable polymer, e.g., cellulose ester polymers and copolymers, insoluble polyurethanes, polyvinyl chloride, polyamides, acrylate polymers and copolymers, ethylenevinylacetate copolymers, vinylpyrrolidone/ethylacetate copolymers, acetal polymers and copolymers, silicone polymers and copolymers, polyesters, polyimides and copolymers and polyetherimides. The biostable polymers may harden and help stabilize other components of the composition without interfering with the character of it. In other aspects, the non-bioabsorbable or biostable polymer is one or more polymers of styrene isobutylene styrene polymers cellulose esters, and/or polystyrene, alkylated polyvinylpyrrolidone.

In exemplary aspects, the surface layer or coating composition may include biostable cellulose esters, e.g., nitrocellulose, insoluble polyurethanes, e.g., those that do not undergo hydrolytic scission in vivo, or acrylic polymers, which may not be water soluble or water swellable.

The wet composition of the present invention may include a polymer at a concentration from about 0.001% to about 25%, 0.5 to 25%, or from about 5 to 20%, 1 to 10%, 2 to 8%, 3 to 7%, 5 to 6%, 2 to 4%, 4 to 6%, 1%, 2%, 3%, 4%, 5%, 6%, 7%, 8%, 9%, 10%, 15%, 20% or 25% or a range between any two of these amounts.

In exemplary embodiments, the present invention may include a skin treatment dry composition that is applied to the skin and contains an amount of polymer from about 50% to 99.9%, or from about 70 to 99%, 73 to 97%, 75 to 95%, 80 to 90%, 73%, 80%, 86%, 87%, 89%, 94%, or 97% or a range between any two of these amounts.

The composition may have one or more active agents. The concentration of active agent(s) depends on several factors, including relative activity of the agent(s), side affects, biological challenge, and other considerations. For example, antibiotics tend to be much more active than many disinfectants, but often encounter drug resistance, which is somewhat less of a problem with disinfectants. Therefore, disinfectants may be preferred, although higher concentrations are often required compared to antibiotics.

The compositions may include an anti-microbial or anti-infective agent, which inhibits infection. "Inhibit infection" refers to the ability of an agent or composition to prevent microorganisms from accumulating and/or proliferating near or at the site of the agent. An agent which inhibits infection is referred to herein as an "anti-infective agent" or "antimicrobial agent." Anti-infective agents include those compounds capable of combating infections resulting from a variety of sources (e.g., bacterial, viral, fungal, and the like). These processes would be expected to occur at a statistically significant level at or near the site of the agent or composition relative to the effect in the absence of the agent or composition.

Representative examples of antimicrobial (anti-infective) agents that may be used in the skin treatment include a quaternary compound, a phenolic compound, an iodinated compound, a silver compound or an acidic-anionic compound. Examples of anti-infective agents include one or more of 2-bromo-2-nitropropane-1,3-diol (e.g., BRONOPOL), Irgasan (TRICLOSAN), polyhexanide (also known as poly-hexamethylene biguanide) (e.g., VANTOCIL IB, COSMOCIL CQ, or BAQUACIL), benzalkonium chloride, benzethonium chloride, cetylpyradinium chloride, stearalkonium chloride, phenol, cresol, aminophenol, iodine, iodide, 8-hydroxyquinolone, and chlorhexidine.

The present invention may include a wet composition containing anti-infective or antimicrobial agents in amounts, for example, from about 0.001% to 50%, 0.5% to 30%, 3% to 27%, or about 3%, 6%, 11%, 13%, 17%, 20%, 25% or 27% w/w or a range between any two of these amounts. These amounts may be for individual agents, or as the sum of several agents.

The wet composition, formulation or solution may include anti-infective or antimicrobial agents at a concentration from about 0.001 to 50%, 0.001 to 8.0%, 0.5 to 5.5%, 0.01 to 1.4%, 0.1-2%, 0.2-1.0%, 0.2%, 0.3%, 0.4%, 0.5%, 0.6%, 0.7%, 0.8%, 0.9%, 1.0%, 1.5%, 2.0%, 2.5%, 3.0%, 3.5%, 4.0%, 4.5%, 5.0%, or 5.5% w/w or a range between any two of these amounts. In some embodiments, the skin treatment dry composition, which is applied to the skin may include about 0.01% to about 8.0% anti-infective agent.

In exemplary embodiments, the skin treatment composition or solution may further include buffers, colorants, surfactants and other components that are biocompatible and do not interfere with the other components or properties in the composition. An example of a surfactant is Tween 80, e.g., 1.00% w/w Tween 80 aq. Examples of colorants may include Gentian Violet (Hucker Formula) and/or dimethylmethylene blue. In other exemplary embodiments, Gentian Violet (Hucker Formula) may be used as an anti-infective agent as well as a colorant.

In some embodiments of the invention, the pH of the composition may be from about 2.0 to 7.0, 2.0 to 6.0, 2.5 to 5, 2.5 to 4, 2.5 to 3.0, or about 3.0.

The composition may also include additional therapeutic agents (referred to synonymously herein as drugs or bioactive agents). These agents include bactericides, antibiotics, antivirals, antiseptics, antineoplastics, anticancer compounds, antifungals, anti-yeast, and/or anti-fibrosis, anti-scarring agents (e.g., mycophenoloic acid), and/or anti-inflammatory agents or other bioactive or therapeutic agents that are suitable for human use. The composition may include from about 0.01 to 8.0% or 0.5 to 5.5% for each of the above agents. Other examples of bioactive agents which have been shown to have anti-microbial (anti-infective) characteristics, in addition to other therapeutic uses, may be used in the present compositions.

An example of an anti-infective agent is a chemotherapeutic agent. Numerous chemotherapeutic agents have been identified that have potent antimicrobial activity at extremely low doses. Exemplary agents include anthracyclines (e.g., doxorubicin and mitoxantrone), fluoropyrimidines (e.g., 5-fluorouracil (5-FU)), folic acid antagonists (e.g., methotrexate), podophylotoxins (e.g., etoposide), camptothecins, hydroxyureas, and platinum complexes (e.g., cisplatin), and/or analogs or derivatives thereof.

Exemplary anthracyclines include doxorubicin, daunorubicin, idarubicin, epirubicin, pirarubicin, zorubicin, carubicin, anthramycin, mitoxantrone, menogaril, nogalamycin, aclacinomycin A, olivomycin A, chromomycin $A_3$, plicamycin, FCE 23762, a doxorubicin derivative, annamycin, ruboxyl, anthracycline disaccharide doxorubicin analog, 2-pyrrolinodoxorubicin, disaccharide doxorubicin analogs, 4-demethoxy-7-O-[2,6-dideoxy-4-O-(2,3,6-trideoxy-3-amino-alpha-L-lyxo-h-exopyranosyl)-alpha-L-lyxo-hexopyranosyl]adriamicinone doxorubicin disaccharide analog, 2-pyrrolinodoxorubicin, morpholinyl doxorubicin analogs, enaminomalonyl-beta-alanine doxorubicin derivatives, cephalosporin doxorubicin derivatives, hydroxyrubicin, methoxymorpholino doxorubicin derivative, (6-maleimidocaproyl)hydrazone doxorubicin derivative, N-(5,5-diacetoxypent-1-yl) doxorubicin, FCE 23762 methoxymorpholinyl doxorubicin derivative, N-hydroxysuccinimide ester doxorubicin derivatives, polydeoxynucleotide doxorubicin derivatives, morpholinyl doxorubicin derivatives, mitoxantrone doxorubicin analog, AD198 doxorubicin analog, 4-demethoxy-3'-N-trifluoroacetyldoxorubicin, 4'-epidoxorubicin, alkylating cyanomorpholino doxorubicin derivative, deoxydihydroiodooxorubicin, adriblastin, 4'-deoxydoxorubicin, 4-demethoxy-4'-o-methyldoxorubicin, 3'-deamino-3'-hydroxydoxorubicin, 4-demethoxy doxorubicin analogs, N-L-leucyl doxorubicin derivatives, 3'-deamino-3'-(4-methoxy-1-piperidinyl) doxorubicin derivatives, 3'-deamino-3'-(4-mortholinyl) doxorubicin derivatives, 4'-deoxydoxorubicin and 4'-o-methyldoxorubicin, aglycone doxorubicin derivatives, SM 5887, MX-2, 4'-deoxy-13(S)-dihydro-4'-iododoxorubicin, morpholinyl doxorubicin derivatives, 3'-deamino-3'-(4-methoxy-1-piperidinyl) doxorubicin derivatives, doxorubicin-14-valerate, morpholinodoxorubicin, 3'-deamino-3'-(3"-cyano-4"-morpholinyl doxorubicin, 3'-deamino-3'-(3"-cyano-4"-morpholinyl)-13-dihydoxorubicin, (3'-deamino-3'-(3"-cyano-4"-morpholinyl) daunorubicin, 3'-deamino-3'-(3"-cyano-4"-morpholinyl)-3-dihydrodaunorubicin, 3'-deamino-3'-(4"-morpholinyl-5-iminodoxorubicin, 3'-deamino-3'-(4-methoxy-1-piperidinyl) doxorubicin derivatives, and 3-deamino-3-(4-morpholinyl) doxorubicin derivatives.

Exemplary fluoropyrimidine analogs include 5-fluorouracil, or an analog or derivative thereof, including carmofur, doxifluridine, emitefur, tegafur, and floxuridine. Other exemplary fluoropyrimidine analogs include 5-FudR (5-fluorodeoxyuridine), or an analog or derivative thereof, including 5-iododeoxyuridine (5-IudR), 5-bromodeoxyuridine (5-BudR), fluorouridine triphosphate (5-FUTP), and fluorodeoxyuridine monophosphate (5-dFUMP). Other representative examples of fluoropyrimidine analogs include N3-alkylated analogs of 5-fluorouracil, 5-fluorouracil derivatives with 1,4-oxaheteroepane moieties, 5-fluorouracil and nucleoside analogs, cis- and trans-5-fluoro-5,6-dihydro-6-alkoxyuracil, cyclopentane 5-fluorouracil analogs, A-OT-fluorouracil, N4-trimethoxybenzoyl-5'-deoxy-5-fluorocytidine and 5'-deoxy-5-fluorouridine, 1-hexylcarbamoyl-5-fluorouracil, B-3839, uracil-1-(2-tetrahydrofuryl)-5-fluorouracil, 1-(2'-deoxy-2'-fluoro-.beta.-D-arabinofuranosyl)-5-fluorouracil, doxifluridine, 5'-deoxy-5-fluorouridine, 1-acetyl-3-O-toluyl-5-fluorouracil, 5-fluorouracil-m-formylbenzene-sulfonate, N'-(2-furanidyl)-5-fluorouracil and 1-(2-tetrahydrofuryl)-5-fluorouracil.

Exemplary folic acid antagonists include methotrexate or derivatives or analogs thereof, including edatrexate, trimetrexate, raltitrexed, piritrexim, denopterin, yomudex, pteropterin. Other representative examples include 6-S-aminoacyloxymethyl mercaptopurine derivatives, 6-mercaptopurine (6-MP), 7,8-polymethyleneimidazo-1,3,2-diazaphosphorines, azathioprine, methyl-D-glucopyranoside mercaptopurine derivatives and s-alkynyl mercaptopurine derivatives, indoline ring and a modified ornithine or glutamic acid-bearing methotrexate derivatives, alkyl-substituted benzene ring C bearing methotrexate derivatives, benzoxazine or benzothiazine moiety-bearing methotrexate derivatives, 10-deazaaminopterin analogs, 5-deazaaminopterin and 5,10-dideazaaminopterin methotrexate analogs, indoline moiety-bearing methotrexate derivatives, lipophilic amide methotrexate derivatives, L-threo-(2S,4S)-4-fluoroglutamic acid and DL-3,3-difluoroglutamic acid-containing methotrexate analogs, methotrexate tetrahydroquinazoline analog, N-(alpha-aminoacyl) methotrexate derivatives, biotin methotrexate derivatives, D-glutamic acid or D-erythrou, threo-4-fluoroglutamic acid methotrexate analogs, beta,gamma-methano methotrexate analogs, 10-deazaaminopterin (10-EDAM) analog, gamma-tetrazole methotrexate analog, N-(L-.alpha.-aminoacyl) methotrexate derivatives, meta and ortho isomers of aminopterin, hydroxymethylmethotrexate, gamma-fluoromethotrexate, polyglutamyl methotrexate derivatives, gem-diphosphonate methotrexate analogs, alpha- and gamma-substituted methotrexate analogs, 5-methyl-5-deaza methotrexate analogs, N-delta-acyl-N-alpha-(4-amino-4-deoxypteroyl)-L-ornithine derivatives, 8-deaza methotrexate analogs, acivicin methotrexate analog, polymeric platinol methotrexate derivative, methotrexate-gamma-dimyristoylphophatidylethanolamine, methotrexate polyglutamate analogs, poly-gamma-glutamyl methotrexate derivatives, deoxyuridylate methotrexate derivatives, iodoacetyl lysine methotrexate analog, 2-omega-diaminoalkanoid acid-containing methotrexate analogs, polyglutamate methotrexate derivatives, 5-methyl-5-deaza analogs, quinazoline methotrexate analog, pyrazine methotrexate analog, cysteic acid and homocysteic acid methotrexate analogs, gamma-tert-butyl methotrexate esters, fluorinated methotrexate analogs, folate methotrexate analog, phosphonoglutamic acid analogs, poly (L-lysine) methotrexate conjugates, dilysine and trilysine methotrexate derivates, 7-hydroxymethotrexate, poly-.gamma.-glutamyl methotrexate analogs, 3',5'-dichloromethotrexate, diazoketone and chloromethylketone methotrexate analogs, 10-propargylaminopterin and alkyl methotrexate homologs, lectin derivatives of methotrexate, polyglutamate methotrexate derivatives, halogentated methotrexate derivatives, 8-alkyl-7,8-dihydro analogs, 7-methyl methotrexate derivatives and dichloromethotrexate, lipophilic methotrexate derivatives and 3',5'-dichloromethotrexate, deaza amethopterin analogs, MX068 and cysteic acid and homocysteic acid methotrexate analogs.

Exemplary podophyllotoxins include etoposide, teniposide, Cu(II)-VP-16 (etoposide) complex, pyrrolecarboxamidino-bearing etoposide analogs, 4-beta-amino etoposide analogs, .gamma.-lactone ring-modified arylamino etoposide analogs, N-glucosyl etoposide analog, etoposide A-ring analogs, 4'-deshydroxy-4'-methyl etoposide, pendulum ring etoposide analogs and E-ring desoxy etoposie analogs.

Exemplary camptothecins include topotecan, irinotecan (CPT-11), 9-aminocamptothecin, 21-lactam-20(S)-camptothecin, 10,11-methylenedioxycamptothecin, SN-38, 9-nitrocamptothecin, and 10-hydroxycamptothecin.

Exemplary platinum complexes include complexes of Pt(II) or Pt(IV), cisplatin, carboplatin, oxaliplatin, and miboplatin. Other representative examples of platinum compounds include $(CPA)_2Pt[DOLYM]$ and $(DACH)Pt[DOLYM]$cisplatin, Cis-$[PtCl_2(4,7-H-5-methyl-7-oxo]1,2,4$ [triazolo[1,5-a]pyrimidine)$_2$], [Pt(cis-1,4-DACH)(trans-$Cl_2$) (CBDCA)] •½MeOH cisplatin, 4-pyridoxate diammine hydroxy platinum, Pt(II) •Pt(II)(Pt$_2$[NHCHN(C(CH$_2$)(CH$_3$))]$_4$), 254-S cisplatin analog, o-phenylenediamine ligand bearing cisplatin analogs, trans, cis-[Pt(OAc)$_2$I$_2$(en)], estrogenic 1,2-diarylethylenediamine ligand (with sulfur-containing amino acids and glutathione) bearing cisplatin analogs, cis-1,4-diaminocyclohexane cisplatin analogs, 5' orientational isomer of cis-[Pt(NH$_3$)(4-aminoTEMP-O){d (GpG)}], chelating diamine-bearing cisplatin analogs, 1,2-diarylethyleneamine ligand-bearing cisplatin analogs, (ethylenediamine)platinum(II) complexes, CI-973 cisplatin analog, cis-diaminedichloroplatinum(II) and its analogs cis-1,1-cyclobutanedicarbosylato(2R)-2-methyl-1,4-butanediaminoplatinum(II) and cis-diammine(glycolato)platinum, cis-amine-cyclohexylamine-dichloroplatinum(II), gem-diphosphonate cisplatin analogs, (meso-1,2-bis(2,6-dichloro-4-hydroxyplenyl)ethylenediamine) dichloroplatinum(II), cisplatin analogs containing a tethered dansyl group, platinum(II) polyamines, cis-(3H)dichloro(ethylenediamine) platinum(II), trans-diamminedichloroplatinum(II) and cis-(Pt(NH$_3$)$_2$(N$_3$-cytosine)Cl), 3H-cis-1,2-diaminocyclohexanedichloroplatinum(II) and 3H-cis-1,2-diaminocyclohexanemalonatoplatinum (II), diaminocarboxylatoplatinum, trans-(D,1)-1,2-diaminocyclohexane carrier ligand-bearing platinum analogs, aminoalkylaminoanthraquinone-derived cisplatin analogs, spiroplatin, carboplatin, iproplatin and JM40 platinum analogs, bidentate tertiary diamine-containing cisplatinum derivatives, platinum(II), platinum(IV), cis-diammine(1,1-cyclobutanedicarboxylato-)platinum(II) (carboplatin, JM8) and ethylenediamminemalonatoplatinum(II) (JM40), JM8 and JM9 cisplatin analogs, (NPr4)2((PtCL4).cis-(PtCl12-(NH2Me)2)), aliphatic tricarboxylic acid platinum complexes, and cis-dichloro(amino acid)(tert-butylamine)platinum(II) complexes.

In some embodiments, the anti-infective agent may be benzalkonium heparinate or sodium heparin. In other aspects of the invention, the composition does not contain any ethylenediamine tetraacetic acid (EDTA).

In exemplary embodiments, the composition may include chemotherapeutic, antimicrobial (anti-infective) agents including but not limited to: anthracyclines (e.g., doxorubicin and mitoxantrone), fluoropyrimidines (e.g., 5-FU), folic acid antagonists (e.g., methotrexate), podophylotoxins (e.g., etoposide), camptothecins, hydroxyureas, and platinum complexes (e.g., cisplatin), and/or analogs or derivatives thereof. For example, such agents may be used in amounts that range from about 50% to 30%, 20%, 10%, 5%, or even less than 1% of the amount typically used in a single chemotherapeutic systemic dose application.

In some aspects, the skin treatment composition may include a therapeutic agent that inhibits fibrosis or scarring. "Fibrosis," or "scarring," or "fibrotic response" refers to the formation of fibrous (scar) tissue in response to injury or medical intervention. Therapeutic agents which inhibit fibrosis or scarring are referred to herein as "fibrosis-inhibiting agents", "anti-fibrosis agents", "fibrosis-inhibitors", "anti-scarring agents", and the like, where these agents inhibit fibrosis through one or more mechanisms including: inhibiting inflammation or the acute inflammatory response, inhibiting migration or proliferation of connective tissue cells (such as fibroblasts, smooth muscle cells, vascular smooth muscle cells), inhibiting angiogenesis, reducing extracellular matrix (ECM) production or promoting ECM breakdown, and/or inhibiting tissue remodeling.

For example, anti-scarring or fibrosis inhibiting agents may be incorporated to improve the function of the composition, particularly when applied to a site of insertion or implantation of a device e.g. by enhancing resistance to protein absorption. Representative examples of fibrosis inhibiting agents which can inhibit pathological processes in a treatment or application site include, but are not limited to, the following classes of compounds: anti-inflammatory agents e.g., dexamethasone, cortisone, fludrocortisone, prednisone, prednisolone, 6-alpha-methylprednisolone, triamcinolone, and betamethasone), MMP inhibitors (e.g., batimistat, marimistat, and TIMP's); cytokine inhibitors (e.g., chlorpromazine, mycophenolic acid, rapamycin, 1-alpha-hydroxy vitamin D$_3$), IMPDH (e.g., inosine monophosplate dehydrogenase) inhibitors (e.g., mycophenolic acid, ribaviran, aminothiadiazole, thiophenfurin, tiazofurin, viramidine), p38 MAP kinase inhibitors (MAPK) (e.g., GW-2286, CGP-52411, BIRB-798, SB220025, RO-320-1195, RWJ-67657, RWJ-68354, SCIO-469), and immunomodulatory agents (rapamycin, everolimus, ABT-578, azathioprine azithromycin, analogs of rapamycin, including tacrolimus and derivatives thereof and everolimus and derivatives thereof, and sirolimus and analogs and derivatives thereof (e.g., ABT-578).

In some aspects, agents include those that inhibit fibrosis such as paclitaxel, sirolimus, everolimus, vincristine, biolimus, ABT-578, cervistatin, simvastatin, methylprednisolone, dexamethasone, actinomycin-D, angiopeptin, L-arginine, estradiol, 17-beta-estradiol, tranilast, methotrexate, batimistat, halofuginone, BCP-671, QP-2, lantrunculin D, cytochalasin A, nitric oxide, and analogs and derivatives thereof.

Other exemplary drugs that may be included in the compositions of the invention include tyrosine kinase inhibitors, such as imantinib, ZK-222584, CGP-52411, CGP-53716, NVP-AAK980-NX, CP-127374, CP-564959, PD-171026, PD-173956, PD-180970, SU-0879, and SKI-606. Other examples of MMP inhibitors include nimesulide, PKF-241-466, PKF-242-484, CGS-27023A, SAR-943, primomastat, SC-77964, PNU-171829, AG-3433, PNU-142769, SU-5402, and dexlipotam; p38 MAP kinase inhibitors such as CGH-2466 and PD-98-59; immunosuppressants such as argyrin B, macrocyclic lactone, ADZ-62-826, CCI-779, tilomisole, amcinonide, FK-778, AVE-1726, and MDL-28842; and cytokine inhibitors such as TNF-484A, PD-172084, CP-293121, CP-353164, and PD-168787. Other examples include NFKB inhibitors, such as, AVE-0547, AVE-0545, and IPL-576092 and HMGCoA reductase inhibitors, such as, pravestatin, atorvastatin, fluvastatin, dalvastatin, glenvastatin, pitavastatin, CP-83101, U-20685, apoptosis antagonists (e.g., troloxamine, TCH-346 (N-methyl-N-propargyl-10-aminomethyldibenzo(b,f)oxepin), caspase inhibitors (e.g., PF-5901 (alpha-pentyl-3-(2-quinolinyl-methoxy)benzenemethanol), and JNK inhibitor (e.g., AS-602801).

In other embodiments, the skin treatment composition may further include a corticosteroid, such as synthetic or natural corticosteroids, e.g., dexamethasone, alclometasone dipropionate, amcinonide, betamethasone, clobetasol proprionate, clocortolone pivalate, cortisone, hydrocortisone, desonide, desoximetasone, diflorasone diacetate, fluocinolone acetonide, fluocinonide, fluandrenolide, halcinonide, methylprednisolone, mometasone furoate, and triamcinolone.

In other embodiments, the skin treatment composition may contain a non-steroidal anti-inflammatory drug (NSAID), such as aspirin, phenylbutazone, indomethacin, sulindac, tolmetin, ibuprofen, piroxicam, fenamates, acetaminophen and phenacetin.

The composition may further include one or more active agent(s) selected from the group consisting of bactericides, antibiotics, antiviral, antiseptics, antineoplastics, anti-inflammatory agents, analgesic agents, anticancer compounds, antifungal, anti-yeast, anti-fibrosis, and anti-scarring agents suitable for topical human use. In some embodiments, the composition may include one or more antiseptic agent, a quaternary ammonium compound, and/or a nonsteroidal anti-inflammatory agent. In yet other embodiments, the composition includes an anti-infective agent selected from the group consisting of a quaternary compound, a phenolic compound, an iodinated compound, a silver compound or an acidic-anionic compound. In other aspects, the anti-infective agent may be selected from the group polyhexamethylene biguanide (BAQUACIL), benzalkonium chloride, benzethonium chloride, cetylpyradinium chloride, stearalkonium chloride, phenol, cresol, aminophenol, iodine, iodide, 8-hydroxyquinolone or chlorhexidine.

In other embodiments, the skin treatment composition may contain an antibiotic compound or compounds. Table 1 below lists exemplary antibiotics that can be included in the skin treatment compositions, sorted by class. The highest division is between antibiotics which are bactericidal and those which are bacteriostatic. Bactericidals kill bacteria directly where bacteriostatics prevent bacteria from dividing.

TABLE 1

| Generic name | Brand names | Common uses[2] | Possible side effects[2] | Mechanism of action |
|---|---|---|---|---|
| Aminoglycosides ||||| 
| Amikacin | Amikin | Infections caused by Gram-negative bacteria, such as *Escherichia coli* and *Klebsiella* particularly *Pseudomonas aeruginosa*. Effective against Aerobic bacteria (not obligate/facultative anaerobes) and tularemia. | Hearing loss Vertigo Kidney damage | Binding to the bacterial 30S ribosomal subunit (some work by binding to the 50S subunit), inhibiting the translocation of the peptidyl-tRNA from the A-site to the P-site and also causing misreading of mRNA, leaving the bacterium unable to synthesize proteins vital to its growth. |
| Gentamicin | Garamycin ||||
| Kanamycin | Kantrex ||||
| Neomycin | Mycifradin ||||
| Netilmicin | Netromycin ||||
| Streptomycin |  ||||
| Tobramycin | Nebcin ||||
| Paromomycin | Humatin ||||
| Ansamycins ||||| 
| Geldanamycin |  | Experimental, as antitumor antibiotics |||
| Herbimycin |  ||||
| Carbacephem ||||| 
| Loracarbef | Lorabid |  |  | prevents bacterial cell division by inhibiting cell wall synthesis. |

TABLE 1-continued

Antibiotics by class

| Generic name | Brand names | Common uses[2] | Possible side effects[2] | Mechanism of action |
|---|---|---|---|---|
| Carbapenems | | | | |
| Ertapenem | Invanz | Bactericidal for both Gram-positive and Gram-negative organisms and therefore useful for empiric broad-spectrum antibacterial coverage. (Note MRSA resistance to this class.) | Gastrointestinal upset and diarrhea Nausea Seizures Headache Rash and allergic reactions | Inhibition of cell wall synthesis |
| Doripenem | Finibax | | | |
| Imipenem/Cilastatin | Primaxin | | | |
| Meropenem | Merrem | | | |
| Cephalosporins (First generation) | | | | |
| Cefadroxil | Duricef | | Gastrointestinal upset and diarrhea Nausea (if alcohol taken concurrently) Allergic reactions | Same mode of action as other beta-lactam antibiotics: disrupt the synthesis of the peptidoglycan layer of bacterial cell walls. |
| Cefazolin | Ancef | | | |
| Cefalotin or Cefalothin | Keflin | | | |
| Cefalexin | Keflex | | | |
| Cephalosporins (Second generation) | | | | |
| Cefaclor | Ceclor | | Gastrointestinal upset and diarrhea Nausea (if alcohol taken concurrently) Allergic reactions | Same mode of action as other beta-lactam antibiotics: disrupt the synthesis of the peptidoglycan layer of bacterial cell walls. |
| Cefamandole | Mandole | | | |
| Cefoxitin | Mefoxin | | | |
| Cefprozil | Cefzil | | | |
| Cefuroxime | Ceftin, Zinnat | | | |
| Cephalosporins (Third generation) | | | | |
| Cefixime | Suprax | | Gastrointestinal upset and diarrhea Nausea (if alcohol taken concurrently) Allergic reactions | Same mode of action as other beta-lactam antibiotics: disrupt the synthesis of the peptidoglycan layer of bacterial cell walls. |
| Cefdinir | Omnicef, Cefdiel | | | |
| Cefditoren | Spectracef | | | |
| Cefoperazone | Cefobid | | | |
| Cefotaxime | Claforan | | | |
| Cefpodoxime | Vantin | | | |
| Ceftazidime | Fortaz | | | |
| Ceftibuten | Cedax | | | |
| Ceftizoxime | | | | |
| Ceftriaxone | Rocephin | | | |
| Cephalosporins (Fourth generation) | | | | |
| Cefepime | Maxipime | | Gastrointestinal upset and diarrhea Nausea (if alcohol taken concurrently) Allergic reactions | Same mode of action as other beta-lactam antibiotics: disrupt the synthesis of the peptidoglycan layer of bacterial cell walls. |
| Cephalosporins (Fifth generation) | | | | |
| Ceftobiprole | | Used to treat MRSA | Gastrointestinal upset and diarrhea Nausea (if alcohol taken concurrently) Allergic reactions | Same mode of action as other beta-lactam antibiotics: disrupt the synthesis of the peptidoglycan layer of bacterial cell walls. |

TABLE 1-continued

Antibiotics by class

| Generic name | Brand names | Common uses[2] | Possible side effects[2] | Mechanism of action |
|---|---|---|---|---|
| Glycopeptides | | | | |
| Teicoplanin | | | | inhibiting peptidoglycan synthesis |
| Vancomycin | Vancocin | | | |
| Macrolides | | | | |
| Azithromycin | Zithromax, Sumamed, Zitrocin | *Streptococcal* infections, syphilis, respiratory infections, mycoplasmal infections, Lyme disease | Nausea, vomiting, and diarrhea (especially at higher doses) Jaundice | inhibition of bacterial protein biosynthesis by binding irreversibly to the subunit 50S of the bacterial ribosome, thereby inhibiting translocation of peptidyl tRNA. |
| Clarithromycin | Biaxin | | | |
| Dirithromycin | Dynabac | | | |
| Erythromycin | Erythocin, Erythroped | | | |
| Roxithromycin | | | | |
| Troleandomycin | TAO | | | |
| Telithromycin | Ketek | Pneumonia | Visual Disturbance, Liver Toxicity.[3] | |
| Spectinomycin | | Antimetabolite, Anticancer | | |
| Monobactams | | | | |
| Aztreonam | Azactam | | | Same mode of action as other beta-lactam antibiotics: disrupt the synthesis of the peptidoglycan layer of bacterial cell walls. |
| Penicillins | | | | |
| Amoxicillin | Novamox, Amoxil | Wide range of infections; penicillin used for *streptococcal* infections, syphilis, and Lyme disease | Gastrointestinal upset and diarrhea Allergy with serious anaphylactic reactions Brain and kidney damage (rare) | Same mode of action as other beta-lactam antibiotics: disrupt the synthesis of the peptidoglycan layer of bacterial cell walls. |
| Ampicillin | Principen | | | |
| Azlocillin | | | | |
| Carbenicillin | | | | |
| Cloxacillin | Tegopen | | | |
| Dicloxacillin | Dynapen | | | |
| Flucloxacillin | Floxapen | | | |
| Mezlocillin | | | | |
| Meticillin | | | | |
| Nafcillin | | | | |
| Oxacillin | | | | |
| Penicillin | | | | |
| Piperacillin | | | | |
| Ticarcillin | | | | |
| Polypeptides | | | | |
| Bacitracin | | Eye, ear or bladder infections; usually applied directly to the eye or inhaled into the lungs; rarely given by injection | Kidney and nerve damage (when given by injection) | Inhibits isoprenyl pyrophosphate, a molecule which carries the building blocks of the peptidoglycan bacterial cell wall outside of the inner membrane[4] |
| Colistin | | | | Interact with the bacterial cytoplasmic membrane, changing its permeability. |
| Polymyxin B | | | | |

TABLE 1-continued

| | | Antibiotics by class | | |
|---|---|---|---|---|
| Generic name | Brand names | Common uses[2] | Possible side effects[2] | Mechanism of action |
| Quinolones | | | | |
| Ciprofloxacin | Cipro, Ciproxin, Ciprobay | Urinary tract infections, bacterial prostatitis, community-acquired pneumonia, bacterial diarrhea, mycoplasmal infections, gonorrhea | Nausea (rare), irreversible damage to central nervous system (uncommon), tendinosis (rare) | inhibit the bacterial DNA gyrase or the topoisomerase IV enzyme, thereby inhibiting DNA replication and transcription. |
| Enoxacin | Penetrex | | | |
| Gatifloxacin | Tequin | | | |
| Levofloxacin | Levaquin | | | |
| Lomefloxacin | Maxaquin | | | |
| Moxifloxacin | Avelox | | | |
| Norfloxacin | Noroxin | | | |
| Ofloxacin | Floxin, Ocuflox | | | |
| Trovafloxacin | Trovan | Withdrawn | | |
| Grepafloxacin | Raxar | Withdrawn | | |
| Sparfloxacin | Zagam | Withdrawn | | |
| Temafloxacin | Omniflox | Withdrawn | | |
| Sulfonamides | | | | |
| Mafenide | | Urinary tract infections (except sulfacetamide and mafenide); mafenide is used topically for burns | Nausea, vomiting, and diarrhea Allergy (including skin rashes) Crystals in urine Kidney failure Decrease in white blood cell count Sensitivity to sunlight | Folate synthesis inhibition. They are competitive inhibitors of the enzyme dihydropteroate synthetase, DHPS. DHPS catalyses the conversion of PABA (para-aminobenzoate) to dihydropteroate, a key step in folate synthesis. Folate is necessary for the cell to synthesize nucleic acids (nucleic acids are essential building blocks of DNA and RNA), and in its absence cells will be unable to divide. |
| Sulfonamidochrysoidine (archaic) | Prontosil | | | |
| Sulfacetamide | | | | |
| Sulfadiazine | Micro-Sulfon | | | |
| Sulfamethizole | | | | |
| Sulfanilimide (archaic) | | | | |
| Sulfasalazine | Azulfidine | | | |
| Sulfisoxazole | | | | |
| Trimethoprim | Trimpex | | | |
| Trimethoprim-Sulfamethoxazole (Co-trimoxazole) (TMP-SMX) | Bactrim, Septra | | | |
| Tetracyclines | | | | |
| Demeclocycline | Declomycin | Syphilis, chlamydial infections, Lyme disease, mycoplasmal infections, acne rickettsial infections, *malaria *Note: Malaria is caused by a protist and not a bacterium. | Potentially Permanent Gastrointestinal upset Sensitivity to sunlight Potential toxicity to mother and fetus during pregnancy Enamel hypoplasia (staining of teeth) transient depression of bone growth | inhibiting the binding of aminoacyl-tRNA to the mRNA-ribosome complex. They do so mainly by binding to the 30S ribosomal subunit in the mRNA translation complex. |
| Doxycycline | Vibramycin | | | |
| Minocycline | Minocin | | | |
| Oxytetracycline | Terramycin | | | |
| Tetracycline | Sumycin, Achromycin V, Steclin | | | |

TABLE 1-continued

Antibiotics by class

| Generic name | Brand names | Common uses[2] | Possible side effects[2] | Mechanism of action |
|---|---|---|---|---|
| Others | | | | |
| Arsphenamine | Salvarsan | Spirochaetal infections (obsolete) | | |
| Chloramphenicol | Chloromycetin | meningitis, MRSA, topical use, or for low cost internal treatment. Historic: typhus, cholera. gram negative, gram positive, anaerobes | Rarely: aplastic anemia. | Inhibits bacterial protein synthesis by binding to the 50S subunit of the ribosome |
| Clindamycin | Cleocin | acne infections, prophylaxis before surgery | | |
| Lincomycin | Lincocin | acne infections, prophylaxis before surgery | | |
| Ethambutol | Myambutol | Antituberculosis | | |
| Fosfomycin | Monurol | | | |
| Fusidic acid | Fucidin | | | |
| Furazolidone | | | | |
| Isoniazid | I.N.H. | Antituberculosis | | |
| Linezolid | Zyvox | VRSA | | |
| Metronidazole | Flagyl | *Giardia* | | |
| Mupirocin | Bactroban | | | |
| Nitrofurantoin | Macrodantin, Macrobid | | | |
| Platensimycin | | | | |
| Pyrazinamide | | Antituberculosis | | |
| Quinupristin/Dalfopristin | Syncercid | | | |
| Rifampicin (Rifampin in US) | | mostly Gram-positive and mycobacteria | Reddish-orange sweat, tears, and urine | Binds to the β subunit of RNA positive polymerase to inhibit transcription |
| Thiamphenicol | | Gram-negative, Gram-positive, anaerobes. widely used in veterinary medicine. | Lacks known anemic side-effects. | A chloramphenicol it analog. May inhibit bacterial protein synthesis by binding to the 50S subunit of the ribosome |
| Tinidazole | | | | |
| Dapsone | Avlosulfon | Antileprotic | | |
| Clofazimine | Lamprene | Antileprotic | | |

References
1. Pelczar, M.J., Chan, E.C.S. and Krieg, N.R. (1999) "Host-Parasite Interaction; Nonspecific Host Resistance", In: Microbiology Conceptsand Applications, 6th ed., McGraw-Hill Inc., New York, U.S.A. pp. 478-479.
2. For common Uses and possible side effects reference is: Robert Berkow (ed.) *The Merck Manual of Medical Information - Home Edition*. Pocket (September 1999), ISBN 0-671-02727-1.
3. Splete, Heidi; Kerri Wachter (March 2006). "Liver toxicity reported with Ketek". *Internal Medicine News*.
4. Mechanism of Action of Bacitracin: Complexation with Metal Ion and C55-Isoprenyl Pyrophosphate K. John Stone and Jack L. Strominger In some aspects, a therapeutic agent may include anti-infectives such as antibiotics, antiseptics and antiviral agents, analgesics and analgesic combinations, anorexics, antidiarrheal, antihistamines, anti-inflammatory agents, antimigraine preparations, antimotion sickness agents, antinauseants, antineoplastic, antiparkinsonism drugs, antipruritic, antipsychotic, antipyretics, antispasmodics including gastrointestinal and urinary, anticholinergic, sympathomimetic, xanthine derivatives, cardiovascular preparations including calcium channel blockers, beta-blockers, antiarrythmics, antihypertensives, diuretics, vasodilator including general coronary, peripheral and cerebral, central nervous system stimulants including cough and cold preparations, decongestants, diagnostics, hormones, immunosupressives, muscle relaxants, parasympatholytic, parasympathomimetic, psychostimulants, sedatives and tranquilizers.

Other bioactive agents may also be used herein to treat other maladies such as, for example, cancerous skin lesions. Disinfecting agents are useful in the compositions of the instant invention, although classic antibiotic agents may also be used. Agents may be selected for use in anti-infective compositions where resistance has not become such a widespread issue at this time as compared with the classic antibiotics in the current library. Further, many disinfecting agents appear to be more resistant to changes in organisms that lead to resistance. It is thought that many of these agents are effective biocides only at higher concentrations and the mechanisms of their action may have a lesser discrimination index between healthy host tissue and pathological organisms.

Other agents may also be incorporated in the compositions of the instant invention in order to provide further modes of therapeutic action(s). For instance, anticancer agents may be used in the compositions of the instant invention and the favorable enhancement of activity would also prevail for the same reason as with anti-infective agents described above. The concentration gradient between the targeted sites vs. the systemic concentrations of the therapeutic agents would favor efficacy in the malady and reduced side affects because of the reduced systemic concentrations.

The composition may be prepared in a variety of manners, in a variety of topical forms, and along with a variety of components and suitable carriers. For example, these preparations may take the form of a cream, an ointment, a lotion, a gel, a drop formulation, a jelly, a salve, a spray, and a stick.

In some aspects, the components, e.g., the polymer, may provide the composition with constructive modulation of the transdermal properties, as well as contributing to the stability of some of the composition components.

The composition may be applied directly on a site of concern in need of treatment on an individual. The composition may be applied daily, at least once a day, or twice daily basis, or at least three, four, five or six times a day. In some embodiments, the invention relates to a method of treating an area of the skin of an individual, in need of treatment.

A "site of concern" in need of treatment means, for example, a site having a skin or cutaneous condition, or a site that is a target location for inserting a medical device through the skin, that is, an insertion point where a medical device is being inserted. In need of treatment means there are preexisting skin related abnormalities or the area will undergo stress, e.g., a breech or a puncture, due to inserting a medical device, and will require treatment or pretreatment, e.g., to avoid or eliminate infection.

"Inserted" or "insertable" refers to a device for which at least a portion can be or has been introduced into a host. A device such as an implant may be inserted into body tissue, for example, through the skin (percutaneously), and potentially other types of tissue, such as muscle, bone, cartilage, tendons, fascia, and the like, or into a body lumen (e.g., a blood vessel) or cavity. A device is partially inserted when some of the device reaches, or extends to the outside of, a host.

As used herein, "skin" is an organ or the outer covering of the body of an individual and includes multiple layers of ectodermal tissue, including the epidermis, which provides waterproofing and serves as a barrier to infection, the dermis, which serves as a location for the appendages of skin; and the hypodermis, which is the subcutaneous adipose layer. As used herein tissue or cutaneous means of the skin.

In some aspects, the invention relates to a method of treating the skin of an individual, for example on the skin, wherein the individual has a site of concern on the skin in need of treatment. The method includes applying a topical skin treatment composition of the present invention to the site of concern. The composition can include, for example, polyethylene glycol, triclosan, and one or more of a salicylate, bronopol, and an acrylic emulsion.

A skin or cutaneous condition as used herein is any abnormality or malady in the skin of an individual or not healthy skin. A skin condition may include a lesion, cut, wound, bruise, puncture, breech, infection, ulcers, macule, patch, scale, wrinkle, papule, plaque, nodule, vesicle, bulla, pustule, cyst, erosion, ulcer, fissure, wheal, telangiectasia, burrow, scale, crust, lichenification, excoriation, a punctuate, puncture, abrasion, induration, burn, rash, decubital ulcer, such as bed sores or pressure sores, atrophy, or other trauma to the skin.

Various skin conditions are described below, although the descriptions are not intended to vary the meaning of any term as the same would be understood in the art. A macule is a change in surface color, without elevation or depression and, therefore, nonpalpable, which may be well or ill-defined, variously sized, but generally considered less than either 5 or 10 mm in diameter at the widest point. A patch is a large macule equal to or greater than either 5 or 10 mm. Patches may have some subtle surface change, such as a fine scale or wrinkling, but although the consistency of the surface is changed, the lesion itself is not palpable. A papule is a circumscribed, solid elevation of skin with no visible fluid, varying in size from a pinhead to either less than 5 or 10 mm in diameter at the widest point. A plaque has been described as a broad papule, or confluence of papules equal to or greater than 1 cm, or alternatively as an elevated, plateau-like lesion that is greater in its diameter than in its depth. A nodule is morphologically similar to a papule, but is greater than either 5 or 10 mm in both width and depth, and most frequently centered in the dermis or subcutaneous fat. The depth of involvement is what differentiates a nodule from a papule. A vesicle is a circumscribed, fluid-containing, epidermal elevation generally considered less than either 5 or 10 mm in diameter at the widest point. A bulla is a large vesicle described as a rounded or irregularly shaped blister containing serous or seropurulent fluid, equal to or greater than either 5 or 10 mm, depending on one's definition of a vesicle. A pustule is a small elevation of the skin containing cloudy or purulent material usually consisting of necrotic inflammatory cells. A cyst is a cavity containing liquid, semisolid, or solid material. Erosion is a discontinuity of the skin exhibiting incomplete loss of the epidermis, a lesion that is moist, circumscribed, and usually depressed. An ulcer is a discontinuity of the skin exhibiting complete loss of the epidermis and often portions of the dermis and even subcutaneous fat. A fissure is a crack in the skin that is usually narrow but deep. A wheal is a rounded or flat-topped, pale red papule or plaque that is characteristically evanescent, disappearing within 24 to 48 hours. A telangiectasia represents an enlargement of superficial blood vessels to the point of being visible. A burrow appears as a slightly elevated, grayish, tortuous line in the skin, and is caused by burrowing organisms. A scale is dry or greasy laminated masses of keratin that represent thickened stratum corneum. A crust is dried serum, pus, or blood usually mixed with epithelial and sometimes bacterial debris. A lichenification is epidermal thickening characterized by visible and palpable thickening of the skin with accentuated skin markings. An excoriation is a punctate or linear abrasion produced by mechanical means (often scratching), usually involving only the epidermis but not uncommonly reaching the papillary dermis. An induration is dermal thickening causing the cutaneous surface to feel thicker and firmer. Atrophy refers to a loss of tissue, and can be epidermal, dermal, or subcutaneous. With epidermal atrophy, the skin appears thin, translucent, and wrinkled. Dermal or subcutaneous atrophy is represented by depression of the skin.

"Host", "subject", "patient", "individual" and the like are used synonymously to refer to a living being requiring treatment or pretreatment, for example by having a skin condition or into which a device or implant will be inserted or implanted. The host may be a human or non-human animal. In particular embodiments the individual is suffering from or has diabetes, and the skin condition is a diabetes related condition, legion or ulcer, or is an infected site from a needle insertion.

For individuals with diabetes, having too much glucose (sugar) in their blood for a long time can cause serious complications, including skin problems. In fact, as many as a third of individuals with diabetes will have a skin condition related to their disease at some time in their lives. Skin conditions linked to diabetes or diabetes related skin conditions, may include, for example, scleroderma diabeticorum, vitiligo, acanthosis nigricans, cushing syndrome, necrobiosis lipoidica diabeticorum, diabetic dermopathy, digital sclerosis, eruptive xanthomatosis, diabetic blisters (bullosis diabeticorum), disseminated granuloma annulare, bacterial infections, fungal infections, itchy skin, and diabetic foot ulcers (DFU's).

Various conditions are described below, although the descriptions are not intended to vary the meaning of any term as the same would be understood in the art. Scleroderma diabeticorum is a condition that causes a thickening of the skin on the back of the neck and upper back. This condition is rare but can affect individuals with type 2 diabetes. Vitiligo is a condition that affects skin coloration. With vitiligo, the cells that make pigment (the substance that controls skin color) are destroyed, resulting in patches of discolored skin. Vitiligo often affects the chest and abdomen, but may be found on the face around the mouth, nostrils and eyes. This condition is more commonly associated with type 1 diabetes. Acanthosis nigricans is a condition that results in the darkening and thickening of certain areas of the skin especially in the skin folds. The skin becomes tan or brown and is sometimes slightly raised and described as velvety. Most often the condition, which typically looks like a small wart, appears on the sides or back of the neck, the armpits, or under the breast or groin. Occasionally the top of the knuckles will have a particularly unusual appearance. Cushing syndrome is a condition and a skin manifestation of insulin resistance in most individuals. Necrobiosis lipoidica diabeticorum (NLD) is caused by changes in the collagen and fat content underneath the skin. The overlaying skin area becomes thinned and reddened. Most lesions are found on the lower parts of the legs and can ulcerate if subjected to trauma. Lesions have fairly well defined borders between normal skin and affected lesions. Sometimes, NLD is itchy and painful. Diabetic dermopathy is also called shin spots. This condition develops as a result of changes to the blood vessels that supply the skin. Dermopathy appears as a shiny round or oval lesion of thin skin over the front lower parts of the lower legs. Digital sclerosis is a condition in which the skin on your toes, fingers and hands becomes thick, waxy and tight. Stiffness of the finger joints also may occur. Eruptive xanthomatosis is condition that may occur when triglycerides rise to extremely high levels. Severe resistance to insulin makes it difficult for the body to clear the fat from the blood. With extreme elevations in these blood fats, individuals are at risk for pancreatitis, an inflammation of the pancreas. Eruptive xanthomas appear as firm, yellow, waxy pea-like bumps on the skin. The bumps—which are surrounded by red halos and are itchy—usually are found on the face and buttocks. They also can be seen on the back side of the arms and legs as well as in the creases of the extremities. Individuals with diabetes can develop diabetic blisters (bullosis diabeticorum) that resemble burn blisters. These blisters can occur on the fingers, hands, toes, feet, legs or forearms. Disseminated granuloma annulare causes sharply defined, ring or arc-shaped areas on the skin. These rashes most often occur on the fingers and ears, but they can occur on the chest and abdomen. The rash can be red, red-brown or skin colored. Skin infections can be caused by a number of different kinds of bacterial infections affecting the skin. Skin infections with the bacteria known as *Staphylococcus* are more common and more serious in individuals with diabetes which is not under control. These bacteria can cause in 'boils', an inflamed nodule from a hair follicle, which can occur in areas where hair follicles can be irritated. Other infections include styes, which are infections of the glands of the eyelids, and bacterial nail infections. Fungal infections, including a yeast-like fungus called "*Candida albicans*" is responsible for many of the fungal infections affecting individuals with diabetes. Females in particular are prone to infection with this fungus in the vagina. Other commonly seen areas of infection include the corners of the mouth with what is known as "angular cheilitis," which feels like small cuts on the corners of the mouth. Fungus also can occur in between the toes and fingers and in the nails (onychomycosis). This fungus creates itchy, bright red rashes, often surrounded by tiny blisters and scales. These infections most often occur in warm, moist folds of the skin. Three common fungal infections are: jock itch (red, itchy area on the genitals and the inside of the thighs), athlete's foot (affects the skin between the toes), and ringworm (ring-shaped, scaly patches that can itch or blister and appear on the feet, groin, chest and abdomen, scalp or nails). A potentially fatal fungal infection with Mucormycosis is seen in individuals with diabetes. Itching skin, also called pruritus, can have many causes, such as a yeast infection, dry skin or poor blood flow. When itching is caused by poor blood flow, the lower legs and feet are most often affected.

In some embodiments the skin condition may be a skin ulcer, a refractory skin infection, ulceration or infection in a limb, such as a foot.

In some aspects of the invention, the compositions can be used to effectively treat infectious lesions such as Diabetic Foot Ulcers (DFU's). DFU's are refractory skin infections that occur particularly among diabetic patients, and are made more likely because patients typically have neuropathy and reduced blood circulation, particularly at the extremities. Patients with diabetes have a higher incidence of suffering from DFU's. Approximately 15 to 20 percent of the estimated 16 million persons in the United States with diabetes mellitus will be hospitalized with a foot complication at some time during the course of their disease. The most characteristic lesion of the diabetic foot is a mal perforans ulceration, which is also one of the major risk factors for amputation.

The etiology of diabetic foot ulcers usually has many components. DFU's may lead to peripheral sensory neuropathy, trauma, and deformity. Other factors in ulceration are ischemia, callus formation, and edema. Systemic antibiotic therapy is complicated in the case of DFU's, because there are other multiple infectious organisms, thus requiring multiple antibiotic regimens. When infection is present, aerobic and anaerobic cultures should be obtained, followed by initiation of appropriate broad-spectrum antibiotic therapy. The infectious organism population mix may even change during the therapy, thus requiring additional cultures and possible changes in the antibiotic regimen.

As used herein, "topical" or "transdermal" refers to applying a composition directly to the skin by means other than systemic administration to provide targeted, localized, effective concentrations of agents and components. The compositions of the present invention are generally intended for topical application on exterior surfaces of the skin, and for internal surfaces of the skin, such as insertion sites or surgical sites and organs, rather than for systemic application. Typical side effects of systemic administration of agents are reduced with topical administration of the present composition, because the agents are not administered systemically, and the amounts of agents administered, while small, nevertheless achieve higher and more effective drug concentrations within the treated locations or sites of concern. Often virtually undetectable systemic concentrations result, thus reducing drug side effects that are associated with systemic administration of the agents. Thus, enhanced therapy is achieved compared with systemic administration of the same or similar agents. The compositions and methods of the instant invention enable targeted, relatively high local concentrations of the active agents. This also enables for example, the use of anti-infective agents that would not ordinarily be used systemically because of their activities, but which may be useful in targeted applications.

Moreover, in some embodiments, the compositions of the instant invention are formulated to enable the active agents to penetrate the skin or organ or surgical site surfaces, and thus exert enhanced activity compared with systemic administration of the agents. Such penetration is referred to as transdermal. This produces an enhanced activity compared with systemic administration of agents, because of the higher concentrations of the agents at the malady site than what can safely be achieved with systemic administration. This allows the use of various antiseptic agents in the compositions without the adverse affects that would result from systemic administration of an antiseptic agent.

The topical application of the present compositions enable the use of therapeutic agents that are outside of the usual libraries of agents that are used systemically, and for which resistance or side effects is not as prominent an issue. At the same time, the site of concern is exposed to the agents in very effective concentrations, thus achieving efficacious results.

Transdermal delivery of drugs provides many advantages over conventional oral administration. Advantages of transdermal systems include convenience, non-interrupted therapy, improved patient compliance, targeting capabilities, including enabling of higher drug concentrations at the treated malady site than would be tolerated with systemic administration, reversibility of treatment (by removal of the system from the skin), elimination of "hepatic first pass" effect, high degree of control over systemic blood concentrations with consequent reduction of side effects.

Because the compositions of the invention are applied topically, the active agents are able to diffuse into various epithelial and other tissue layers to exert their action(s). The compositions may be applied in surgical and wound sites to resist or prevent infections, or other post-surgical maladies or non-surgical induced lesions, and to assist healing. The compositions may contain agents such as anti-infective agents, anti-cancer agents, anti-inflammatory agents, healing agents and other materials.

The present invention also provides for broad spectrum antimicrobial compositions designed for transdermal and/or topical application. The compositions provide activity against virus, fungus and bacteria (gram negative, gram positive, aerobic and anaerobic). Furthermore, the compositions can diffuse deeply through the skin layers and beyond to provide more efficacious anti-infective therapy throughout the site of concern. Substances that may be administered topically may include the broad classes of compounds normally delivered through body surfaces such as the skin.

In some embodiments, the skin treatment composition may be applied (e.g., by wiping or spraying) onto implantation sites, before closure of the site, to resist infections from potential contamination. "Implanted" refers to a device that is placed completely (i.e., the whole implant resides within the host) or partially within a host. An implant or other device is partially implanted when some part of the device reaches, protrudes, or extends to the outside of a host. The terms "insertable device" and "implantable device" are used somewhat interchangeably.

Insertable medical devices as used herein have a percutaneously insertable surface. In particular embodiments, the insertable surface of the device may have a composition applied onto the device surface prior to the insertion process through the skin treatment composition, wherein the skin treatment composition contains at least one anti-infective or antimicrobial agent and at least one polymer. As used here in the terms "device treatment composition" and "device surface pre-coating compositions" may be used interchangeably.

Without limiting the scope of the invention, insertable or implantable devices may include devices inserted into tissue, e.g., needles, or devices inserted into vessels or cavities, e.g., needles or catheters. Examples of needles are an infusion set or device, a peripheral venous needle, an indwelling infusion needle, a butterfly needle, a subcutaneous access device, an insulin pump needle or a patient controlled analgesia (PCA) pump needle. Examples of catheters are a peripheral venous catheter, an arterial catheter, a central venous catheter (CVC), a dialysis catheter, a peritoneal dialysis catheter, a nephrostomy catheter, a percutaneous cystostomy catheter, an indwelling paracentesis or pleurocentesis catheter or drain, a percutaneous nephrostomy, a cystostomy tube, a spinal or epidural catheter. Such devices may be used, for example, to introduce various materials such as nutrients or therapeutic agents into patients, or to drain material from a patient. Devices that are not intended for infusion purposes, such as sensors, may also be used.

The device may include catheters, e.g., vascular and dialysis catheters; pacemaker leads, e.g., silicone and polyurethane; tubes, e.g., gastroenteric, drain, nasogastric and endotracheal; shunts, e.g., arteriovenous and hydrocephalous; and needles, e.g. insulin pump, fluid administration, amniocenteses and biopsy.

The devices may be those inserted into tissue, such as needles, or those inserted into vessels and cavities, such as catheters, a portion of which is inserted into the body of the patient and a portion of which protrudes outside of the body. The device may be wholly implanted inside of the body of the patient, e.g., completely beneath the skin surface, such as implantable medical devices. These include, e.g., implantable glucose monitoring devices or implantable insulin pumps. Additional examples of implantable devices may include stents, heart valves, cardiac pacemakers, implantable cardioverter defibrillators, grafts (e.g., vascular grafts), ear, nose, or throat implants, urological implants, endotracheal or tracheostomy tubes, CNS shunts, orthopedic implants, and ocular implants. Exemplary embodiments may be devices used to introduce drugs, e.g., insulin using an insulin pump needle, or devices for fluid drainage, e.g., central nervous catheter containing an anti-infective drug, e.g., 5-fluorouracil and/or methotrexate, or antibiotics, e.g. fluoroquinolones or betslactam drugs.

In particular embodiments, the device is an insulin pump needle or a continuous glucose monitor.

In some embodiments of the invention, the site of concern in need of treatment may be an insertion point where a medical device is to be inserted. In exemplary embodiments, the method may include pre-treating the site, i.e., applying the composition to the site to produce a skin treatment layer/coating prior to inserting the device, and then inserting the medical device through the skin treatment layer or coating. In some embodiments, the method includes allowing the solvent to evaporate and dry to produce a skin treatment layer/coating on the skin prior to inserting the device. In absence of such pre-treatment, i.e. formation of a skin treatment layer, a skin condition may result from a breach or a puncture from the insertable medical instrument. For example, an infection may be caused by the breech or the puncture.

In some embodiments, the skin treatment composition of the present invention utilizes the synergistic combination of components of an anti-infective or anti-microbial agent and a polymer in a solvent to provide a flexible adherent film on the skin that effectively reduces contamination such as infections or protein absorption at the insertion site during an extended period of time. The skin treatment composition can utilize components that are of demonstrated biocompatibility.

In some embodiments, the skin treatment composition provides a coating on the skin at the point of insertion and subsequently after the device is inserted, in which the coating provides resistance to protein absorption and/or infectious formation on surfaces of the skin and/or the device. Such resistance is effective to substantially extend patency of the medical devices when inserted or implanted in patients compared with devices inserted or implanted without such a skin treatment.

In particular embodiments, the polymer solution used herein should be of such viscosity and concentration that it is easily spread on the skin surface with a single wipe using, for example, a QTip that is wetted with the composition. The composition can spread evenly, and dry at ambient temperature within one to two or three minutes. The coating should be thin, such as less than 0.5 mm The polymer solution can be thick enough to enable the composition to be comfortable and flexible on the skin while sufficiently coating it and remaining adherent and effective for an extended period of time, as further defined below. After applying the composition to the skin at the point of insertion and as the device is inserted into the patient, the composition may seal the point of insertion.

The skin treatment coating, once applied, may be referred to as a polymer "cuff" that surrounds the device at the point of insertion. In this sense, the cuff is a band of the skin treatment composition formed on the skin that encircles and abuts the part of the device that goes through the skin, extending into and out from the patient. "At the point of insertion" includes the area around the site of insertion, e.g. a few millimeters to a centimeter or so around the insertion point.

Protein absorption or encapsulation is the result of the body's natural process of encapsulating and isolating a foreign substance, such as a device as described above, in order to protect the body. The resulting tissue reaction can interfere or impede device function, e.g., insulin absorption or blood sugar monitoring, resulting in the need to replace the device in shorter periods of time. By providing a composition according to the invention as part of the insertion process, and having anti-protein absorption as well as antimicrobial or anti-infectious characteristics, the incidence of unwanted protein encapsulation and susceptibility to infection is reduced, allowing the device to remain patent and effective for longer periods of time.

The skin treatment layer as formed by application of the inventive compositions can release anti-infective agent when hydrated by exudate from the insertion site or otherwise. For example, if an exudate leaks out or develops at the access site, or the site becomes otherwise wetted, the exudate can be absorbed or hydrated by the skin treatment layer. The skin treatment layer is suitably at least partially hydrophilic to allow water to diffuse through the layer and evaporate after it has been wetted so the skin under the layer can remain dry much of the time. Water or any exudates that leak out of the insertion site will hydrate the skin treatment layer, and cause some amounts of anti-infective agent to be released, which will resist or prevent growth and migration of organisms of the skin flora. Water or exudate can also solubilize or solvate the anti-infective material, which can exert an anti-infective effect at the site, limiting or preventing infection and resisting growth and/or migration of organisms of the skin flora.

The advantageous extended patency of the compositions means that devices may remain inserted and effective for their intended purpose (e.g., infusion, draining, sensing or eluting) for substantially longer periods of time than devices used without such a skin treatment. Generally, it has been observed and understood by those skilled in the art that needles in untreated skin require replacement every two to four days because infections may set in after 2 to 4 days and/or protein absorption/encapsulation may set in after 2 to 5 days. Substantially longer patency can mean an increase of 10% to four fold, or of 1 to 7 days. It can be a period that is longer by at least about 25%, 50%, 75% or double or triple the period for a comparable uncoated device or a coated device without skin treatment. For example, the period can be extended at least a day, two days, three days, four days, five days, a week or 10 days longer. Furthermore, the extended patency of the inserted device leads to reduced device costs and reduced costs of treating many fewer infectious episodes.

In exemplary aspects, the device is inserted and remains patent for at least about 5 days or longer, e.g. 5 to 10 days, 6 to 9 days, 7 to 8 days, 6 days, 7 days, 8 days, 9 days or 10 days, or longer. In other aspects, the point of insertion remains uninfected for at least five days after insertion.

As used herein "drug burden", e.g., insulin burden, refers to the amount of drug, such as insulin, that is required to produce a desired effect, for example the amount of insulin required to accommodate each unit of carbohydrate food. The drug or insulin burden is found to remain relatively stable during the first few days after needle insertion. However, after the device has been inserted for about 4 to 5 days, the drug or insulin burden can begin to escalate, often dramatically, thus making it difficult to control the therapeutic effect such as blood glucose. Without being bound by theory, it is thought that the insulin burden increases as the device remains inserted due to interference with the device or its function, e.g., due to protein absorption/encapsulation as described herein. In some embodiments, when the skin treatment composition of the invention is applied prior to insertion, the composition is effective to both reduce infection at the insertion site and to enable the drug or insulin burden to remain in an effective range during an extended insertion period.

The skin treatment compositions of the present invention provide several advantages. First, as a universal treatment, the compositions may be used with any medical device, without the need to coat the device during manufacture. Coating a medical device may cause regulatory complications such as the need for further regulatory review and approval of such a coated device. Second, the skin treatment allows patients to use significantly fewer devices. For example, a diabetic patient who must replace an insertable device twice weekly uses about around 100 devices per year. A patient using the skin treatment composition can delay replacement to once weekly, reducing consumption to about 50 devices per year, resulting in greatly enhanced convenience and enormous cost savings to the patient, and to any government or private insurer that would pay for the devices.

In other aspects of the invention, the composition may be packaged in a kit. The kit may include the skin treatment composition as described above in one or more packages, vessels or bottles. The kit may further include an absorbent material, such as a swab or an absorbent pad, suitable for holding the composition and wiping the skin of a patient at a site of insertion of a medical device. The absorbent material may be dry or already saturated with the composition.

In other aspects, the kit may further contain the insertable medical device. The device may be coated or uncoated. The composition may contain at least one anti-infective agent, at least one polymer, and a solvent. In some embodiments, the composition may contain a topical skin treatment composition including polyethylene glycol (PEG), triclosan, a solvent, and one or more of a salicylate, bronopol, and an acrylic emulsion.

The kit may further include an absorbent material, such as a swab or an absorbent pad, suitable for holding the pre-coating composition and wiping the device during the insertion process.

In other embodiments, the invention relates to a method for using an insertable medical device by obtaining an insertable medical device, selecting a point of insertion into the tissue of a patient, and treating the tissue of the patient at the point of insertion by applying the skin treatment composition of the invention. In particular embodiments, the composition may contain a topical skin treatment composition including polyethylene glycol (PEG), triclosan, and one or more of a salicylate, bronopol, and an acrylic emulsion and optionally a solvent.

The skin treatment composition may be applied to the insertion site by wiping or spreading the skin treatment composition onto the insertion site. In some aspects, the area is wiped shortly prior to or immediately before insertion. In other aspects, the area is wiped shortly after or immediately following insertion. The skin treatment composition may be coated onto the skin surface where the device projects from the bodily surface in such a way that the skin treatment layer surrounds and abuts the inserted device projecting from the bodily surface.

In other embodiments, after the skin treatment composition is applied to the body surface, it is allowed to dry at room temperature for a brief time, e.g., less than two minutes or from one to two or three minutes, before inserting the device through the dried skin treatment layer. As used herein "dry" refers to substantially or essentially dry or when solvated after being substantially or essentially dry. After the composition is allowed to dry at room temperature to produce an anti-infective skin treatment layer/coating on the skin, then the device is inserted into the patient at the point of insertion through the dried skin treatment layer/coating.

In some embodiments of the invention, the skin treatment composition is placed onto the body surface and the insertable portion of the device is then passed through the layer into the body. The device may be inserted before the skin treatment composition has dried. In other embodiments, the skin treatment composition is applied on the body surface, around the device after the device has been inserted into the body.

In other embodiments of the invention, the skin treatment composition may be applied repeatedly to form two or more layer-forming compositions. A first layer can be applied against the body surface, and preferably is permeable to the antimicrobial agent(s). A second layer may be applied using the same composition, or a different composition. The second layer may contain an antimicrobial agent in a solvated or dry form, such that the antimicrobial agent can permeate through the first layer. In particular aspects, the composition coatings are dried prior to applying subsequent layers.

In some aspects, the device that is inserted can be coated with the skin treatment composition. In other aspects, the device may be uncoated, and prior to insertion is wiped with an absorbent material, such as a swab or pad, containing the skin treatment composition. The coated device is allowed to dry for a brief time, such as less than two minutes or one to two or three minutes, for the coating to dry at room temperature and is then inserted into the patient as a coated device having a surface coating made up of the skin treatment composition of the invention, for example, a composition having polyethylene glycol (PEG), triclosan, a solvent, and one or more of a salicylate, bronopol, and an acrylic emulsion. In other aspects, a skin treatment composition is applied onto a device insertion site and allowed to dry, e.g., for up to one, two, three, four, five or more minutes, whereupon an uncoated device is inserted through the skin treatment layer percutaneously.

EXAMPLES

The examples listed below are illustrative and are not intended to limit the scope of the invention.

In some examples, skin treatments are used to treat conditions, including infectious skin lesions. In other examples, skin treatments are used to prepare insertion sites for insertion of devices such as insulin pump needles or insertable sensors through the skin. In still other examples, skin treatment compositions were applied to the insertion sites and then devices were coated with some of the skin treatment compositions. The skin treatment solutions were coated on insulin pump needles (Medtronic MiniMed PARADIGM® POLYFIN® WITH WINGS bent Needles) and dried for up to three minutes at room temperature just prior to device insertion. About 1.5 cm of the needle may be coated and from about 1.0 to 1.5 cm of the needle was inserted. The needle was already connected to a delivery tube that was connected to a MiniMed Paradigm® insulin pump. The pump used a 3 ml syringe reservoir that was filled with Novolog® U-100 insulin. The insulin pump had the basal rate set at 1.2 units per hour from 4:00 am to 9:00 am, followed by 0.9 units per hour from 9:00 am to 12 noon, followed by 0.6-0.7 units per hour from noon till 4:00 am the following morning. This basal rate produced declining, fasting blood glucose levels in the mornings for a few days after the needle was first inserted into subcutaneous fatty tissue of the abdominal region. Medtronic MiniMed SOF-SENSOR™ Continuous Glucose Sensors were used in the examples involving sensors.

It was observed that for uncoated needles, after two to four days, when not used with the skin treatment, the desirable decline in fasting blood sugar levels ceases, apparently due to protein absorption around the distal portion of the needle, which is interfering with the absorption of the insulin into the surrounding tissue. The blood glucose levels with the uncoated needles began to ascend so rapidly that it became difficult to control the blood glucose levels in or near desirable ranges, and it became necessary to replace the inserted needles. Needles were inserted, and blood glucose levels were recorded on the order of 2 to 6 times per day. After removal, the days of implantation were noted.

The examples were tested by leaving the needle indwelling as long as it remained patent. The insulin pump basal rate was set so that morning-fasting blood glucose readings declined. In many cases, the needle was removed when the fasting blood glucose stopped declining in the mornings. The fact that the fasting, morning blood glucose readings stopped declining was attributed to protein buildup on the needle. This was done to evaluate whether the device could remain indwelling for longer periods without becoming infected, and to demonstrate that blood glucose could still be controlled in reasonable ranges.

For the examples listed below, the amount in grams and weight percentages are based on each component as listed including reagent solvents as applicable.

Example 1

This is an example of a skin treatment that is useful in healing oral infections that lead to gum pain. The composition was rubbed on the affected gum 2-4 times per day for 1-3 days as needed. The infective outbreak was resolved within that time, and pain was eliminated.

| Oral Skin Treatment Composition (010108A) | | |
|---|---|---|
| H2O | 11.03 g (60.21%) | |
| ETOH | 5.02 g (27.40%) | |
| Isopropyl Alcohol | 0.50 g (2.73%) | |
| Acetylsalicylic acid | 0.08 g (0.44%) | heat- 5 min at 60-70° C., it dissolved |
| Triclosan | 0.02 g (0.11%) | 0.02 g heat- 5 min- dissolved |
| Bronopol | 0.02 g (0.11%) | |
| PEG 400 | 0.16 g (0.87%) | |
| PEG 8000 | 1.49 g (8.13%) | |
| Total wet weight | 18.32 g (100.00%) | |
| Total dry weight | 1.77 g (9.7% w/w) | |

Example 2

This composition was applied twice daily for three days, to a swollen facial infection that originated with a gum infection on a dog. The swelling was about the size of a golf ball. The swelling resolved during the three day application period.

| Skin Treatment Composition (0508-07A, 1222-07A version) pH ~3.0 | |
|---|---|
| WATER | 9.15 g (47.08%) |
| RUM (151 PROOF) | 6.65 g (34.21%) |
| 70% IPA | 0.72 g (3.70%) |
| 100% IPA | 1.00 g (5.14%) |
| Salicylic Acid | 0.11 g (0.57%) |
| Triclosan | 0.02 g (0.10%) |
| Bronopol | 0.02 g (0.10%) |
| PEG 400 | 0.28 g (1.44%) |
| PEG 8K | 1.49 g (7.66%) |
| Total wet weight | 19.44 g (100.00%) |
| Total dry weight | 1.92 g (9.9% w/w) |

Example 3

This composition was applied onto infected skin lesions 2-4 times daily over a few days, and was found to reverse the topical infective outbreak, and to reverse the growth. Application of the composition was suspended after 4 days, and the infective lesion continued to heal and left no skin mark after being fully healed.

| Skin Treatment Composition (031709A) pH ~3.0 | | |
|---|---|---|
| Water | 5.50 g (53.29%) | |
| ETOH* | 3.50 g (33.91%) | |
| Salicylic Acid | 0.09 g (0.87%) | Heat 5 min . . . it dissolved |
| Triclosan | 0.01 g (0.10%) | Heat 10 min . . . it dissolved, but became sl opalescent when cooled to RT. Heat to dissolve and add: |
| Bronopol | 0.02 g (0.19%) | dissolved |
| PEG 400 | 0.45 g (4.36%) | dissolved, but turned v sl opalescent at RT |
| PEG 8K | 0.75 g (7.27%) | Heat 10 min. Formed a clear solution and remained clear upon cooling to RT for more than two weeks. |
| Total wet weight | 10.32 g (100.00%) | |
| Total dry weight | 1.32 g (12.8% w/v) | |

*Sigma 459836-100 ML anhydrous, 200 Proof, 99.5%

Example 4

These compositions were applied onto infective skin lesions 2-4 times daily over a few days, and were found to reverse the topical infective outbreak, and to reverse the growth. Application of the composition was suspended after 4 days, and the infective lesions continued to heal and left no skin mark after being fully healed.

| Skin Treatment Composition (041709A, 060409) | | |
|---|---|---|
| PEG 400 | 8.07 g (37.75%) | |
| ETOH, 190 Proof | 3.00 g (14.03%) | |
| Salicylic Acid | 0.24 g (1.12%) | Heat 5 min, it dissolved and remained clear at RT. |
| Triclosan | 0.02 g (0.09%) | It dissolved with 10 min. heat |
| Bronopol | 0.03 g (0.14%) | It dissolved w/o heat |
| Water | 10.02 g (46.87%) | |
| Total wet weight | 21.38 g (100.00%) | |
| Total dry weight | 8.36 g (39.1% w/w) | |

| Skin Treatment Composition 082009A. This is 041709A with IPO in place of ETOH | | |
|---|---|---|
| PEG 400 | 6.51 g (34.59%) | |
| 99% IPA | 2.00 g (10.63%) | |
| Salicylic acid | 0.24 g (1.28%) | |
| Triclosan | 0.02 g (0.11%) | Heat 10 minutes, it dissolved |
| Bronopol | 0.03 g (0.16%) | |
| Water, dist. | 10.02 g (53.23%) | |
| Total wet weight | 18.82 g (100.00%) | |
| Total dry weight | 6.80 g (36.1% w/w) | |

Example 5

This example, along with Examples 6, 7 and 8, shows how some skin treatments can be used as a anti-infective injection site preparations, and further used along with an insertable devices that may be coated with anti-infective compositions.

The insertion site was first wiped using a Q Tip that was wetted with a skin treatment composition (031609A, listed below) and the solvents were allowed to evaporate for two to three minutes to produce a skin treatment coating or cuff. A skin treatment composition (010108A, listed below) was wiped on two sides of the trochar used to place a Medtronic Sof-Sensor™ glucose sensor and dried. The sensor was then placed thru the wiped-on skin treatment cuff. The sensor was removed after six days, and the insertion site showed no signs of infection.

| Skin Treatment Composition (031609A) used as an anti-infective cuff layer | | |
|---|---|---|
| Ethanol | 1.00 g (8.28%) | |
| 2-Butanone (MEK) | 8.02 g (66.38%) | |
| Rhoplex B15-J | 1.00 g (8.28%) | Became vvsl opalescent, near-solution |
| Triclosan | 0.03 g (0.25%) | |
| Bronopol | 0.03 g (0.25%) | |
| PEG 35K | 2.00 g (16.56%) | Heat 20 min at 60-70° C. and shake to dissolve. It formed clear solution. |
| Total wet weight | 12.08 g (100.00%) | |
| Total dry weight | 2.56 g (21.2% w/w) | |

| Skin Treatment Composition (010108A) used as a device coating | | |
|---|---|---|
| H2O | 11.03 g (60.21%) | |
| ETOH | 5.02 g (27.40%) | |
| Isopropyl Alcohol | 0.50 g (2.73%) | |
| Acetylsalicylic acid | 0.08 g (0.44%) | heat- 5 min at 60-70° C., it dissolved |
| Triclosan | 0.02 g (0.11%) | heat- 5 min-dissolved |
| Bronopol | 0.02 g (0.11%) | |
| PEG 400 | 0.16 g (0.87%) | |
| PEG 8000 | 1.49 g (8.13%) | |
| Total wet weight | 18.32 g (100.00%) | |
| Total dry weight | 1.77 g (9.7% w/w) | |

Example 6

This example discloses the use of a wipe-on, antimicrobial skin treatment cuff with an insulin pump infusions needle. Prior to insertion of the insulin pump needle, the insertion site was wiped, using a QTip with the same skin treatment composition, 031609A, which was used in Example 5 above. The pump needle was inserted after 30-40 seconds to allow for solvents to evaporate from the skin layer. Prior to insertion, the pump needle was wiped on two sides with a skin treatment composition, 031709A, listed below, including salicylic acid and no isopropanol. The needle was removed after eight days of insertion, and showed no indications of infection.

| Skin Treatment Composition (031709A) pH 3.0 | | |
|---|---|---|
| Water | 5.50 g (53.30%) | |
| ETOH* | 3.50 g (33.91%) | |
| Salicylic Acid | 0.09 g (0.87%) | Heat 5 min . . . it dissolved |
| Triclosan | 0.01 g (0.10%) | Heat 10 min . . . it dissolved, but became slightly opalescent when cooled to RT. Heat to dissolve and add: |
| Bronopol | 0.02 g (0.19%) | Dissolved |

| Skin Treatment Composition (031709A) pH 3.0 | | |
|---|---|---|
| PEG 400 | 0.45 g (4.36%) | Dissolved, but turned v sl opalescent at RT |
| PEG 8K | 0.75 g (7.27%) | Heat 10 min. Formed a clear solution and remained clear upon cooling to RT for at least) 2 weeks |
| Total wet weight | 10.32 g (100.00%) | |
| Total dry weight | 1.32 g (12.8% w/w). | |

*Sigma 459836-100 ML anhydrous, 200 Proof, 99.5%

Example 7

This example shows how a skin treatment can be used as an anti-infective injection site preparation, and further used along with an infusion needle that is also coated with an anti-infective composition. An insulin pump needle was wiped on two sides using a QTip wetted with an anti-infective skin treatment, 041709A, listed below, and allowed to dry at room temperature for 60 seconds before insertion. The insertion site was previously coated using a QTip with skin treatment composition, 032909A, listed below, that had been allowed to dry at room temperature for two minutes. This composition produces a more flexible, less deciduous skin treatment than composition 031609A in Examples 5 and 6. The needle was inserted thru the treated insertion site, and left indwelling for seven days. There were no indications of infection when the needle was removed.

| Skin Treatment Composition (032909A) | | |
|---|---|---|
| ETOH | 0.50 g (7.12%) | |
| MEK | 4.50 g (64.10%) | |
| Triclosan | 0.01 g (0.14%) | |
| Rhoplex B15-J | 1.01 g (14.39%) | Heat 10 minutes, it formed a clear solution. |
| PEG 35K | 1.00 g (14.25%) | Heat 20 minutes with intermittent agitation It formed a clear solution |
| Total wet weight | 7.02 g (100.00%) | |
| Total dry weight | 1.52 g (21.7% w/w) | |

| Skin Treatment Composition (041709A) | | |
|---|---|---|
| PEG 400 | 6.50 g (30.39%) | |
| ETOH, 190 Proof | 2.00 g (9.35%) | |
| Salicylic Acid | 0.24 g (1.12%) | Heat 5 min, it dissolved, and remained clear at RT. |
| Triclosan | 0.02 g (0.09%) | It dissolved with 10 min. heat |
| Bronopol | 0.02 g (0.09%) | It dissolved w/o heat |
| Water | 10.03 g (46.89%) | It became vv sl opalescent, Add: |
| PEG 400 | 1.05 g (4.91%) | It was still vv sl opalescent, Add: |
| PEG 400 | 0.53 g (2.48%) | It was still vv sl opalescent, Add: |

-continued

| Skin Treatment Composition (041709A) | | |
|---|---|---|
| ETOH | 1.00 g (4.68%) | It formed a clear solution. |
| Total wet weight | 21.39 g (100.00%) | |
| Total dry weight | 8.36 g (39.08% w/w) | |

Example 8

An insulin pump needle was wiped on two sides using a QTip with skin treatment 010108A, listed below, and allowed to dry for 60 seconds at room temperature before device insertion. The insertion site had previously been coated with skin treatment composition 051609A, listed below, and allowed to dry at room temperature before device insertion. This combination of coated needle and skin treatment showed no infection after seven indwelling days.

| Skin Treatment Composition (010108A) | |
|---|---|
| H2O | 11.03 g (60.21%) |
| ETOH | 5.02 g (27.40%) |
| IPA* | 0.50 g (2.73%) |
| Acetylsalicylic acid | 0.08 g (0.44%) |
| Triclosan | 0.02 g (0.11%) |
| Bronopol | 0.02 g (0.11%) |
| PEG 400 | 0.16 g (0.87%) |
| PEG 8000 T = .77 | 1.49 g (8.13%) |
| Total wet | 18.32 g (100.00%) |
| Total dry | 1.77 g (9.7% w/w) |

| Skin Treatment Composition (051609A) | |
|---|---|
| ETOH | 0.50 g (7.02%) |
| ACETONE | 4.52 g (63.50%) |
| TRICLOSAN | 0.10 g (1.40%) |
| Rhoplex B15-J | 1.00 g (14.04%) |
| PEG 35K | 1.00 g (14.04%) |
| Total wet | 7.12 g (100.00%) |
| Total dry | 1.60 g (22.5% w/w) |

Example 9

In this example, it is shown that the skin treatment composition used in Example 8, 051609A, when coated on the skin at the needle insertion site before insertion, the effects of infection resistance and protein absorption around the inserted device are still maintained, without the need to coat the device.

The skin treatment composition used in EXAMPLE 8, 051609A, was coated on a soft skin insertion site, and allowed to dry. An uncoated insulin pump needle was inserted, and was left indwelling for seven/eight days. The procedure was continued weekly for an entire month.

Results are disclosed in the table below. It is clear that the insulin burden was not unduly increased throughout indwelling periods of up to eight days, and that control of blood glucose was not compromised, and was indeed maintained throughout the entire period.

30 Day Blood Glucose Av.=106 mg/dl as of Aug. 2, 2009

A Life Scan One Touch® Ultra blood glucose meter was used to calibrate the Medtronic SOF-Sensor™ continuous glucose sensor that was used during these trials. The One Touch Ultra meter is able to provide a 30 day average for the last 30 days of readings on the meter. The 30 day average cited above for the date of Aug. 2, 2009, was the 30 day period that corresponds to the data provided in Table 2 in this example.

No infections developed during any of these insertions cycles, even after eight days insertion. Medtronic Paradigm® pump with Novolog® 100 u/ml Insulin.

This table lists the daily bolus totals for the month of July, 2009.

TABLE 2

DAILY BOLUS TOTAL vs. INDWELLING DAYS

| INDWELLING DAYS-1 | WEEK OF 7/4-20 | WEEK OF 7/11-7.5 | WEEK OF 7/18-12 | WEEK OF 7/25 -10 |
|---|---|---|---|---|
| -2 | -9 | -11 | -8 | -7 |
| -3 | -8 | -5 | -18 | -9 |
| -4 | -17 | -17 | -13 | -7.7 |
| -5 | -12 | -7 | -10 | -10 |
| -6 | -11.6 | -10.5 | -13.4 | -5.5 |
| -7 | -18 | -17 | -19 | -8.5 |
| -8 | N/D | N/D | N/D | -13.1 |

Example 10

This composition was applied onto infective skin lesions 2-4 times daily over a few days, and was found to reverse the topical infective outbreak, and to reverse the growth. Application of the composition was suspended after 4 days, and the infective lesions continued to heal and left no skin mark after being fully healed.

| Skin Treatment Composition 082009A pH ~3.0 | | |
|---|---|---|
| PEG 400 | 6.51 g (34.59%) | |
| 99% IPA | 2.00 g (10.63%) | |
| Salicylic acid | 0.24 g (1.28%) | |
| Triclosan | 0.02 g (0.11%) | Heat 10 minutes, it dissolved |
| Bronopol | 0.03 g (0.16%) | |
| Water, dist. | 10.02 g (53.23%) | |
| Total wet weight | 18.82 g (100.00%) | |
| Total dry weight | 6.80 g (36.1% w/w) | |

Example 11

This composition was applied onto infective skin lesions 2-4 times daily over a few days, and was found to reverse the topical infective outbreak, and to reverse the growth. Application of the composition was suspended after 4 days, and the infective lesions continued to heal and left no skin mark after being fully healed.

| 082009C This is 082009A pH ~2.5-3.0 | | |
|---|---|---|
| PEG 400 | 6.51 g (34.46%) | |
| 99% IPA | 2.01 g (10.64%) | |
| Salicylic acid | 0.24 g (1.27%) | |
| Triclosan | 0.04 g (0.21%) | Heat 10 minutes, it dissolved |

-continued

| | 082009C This is 082009A pH ~2.5-3.0 | |
|---|---|---|
| Bronopol | 0.05 g | (0.26%) |
| Water, dist. | 10.04 g | (53.15%) |
| | 18.89 g | (100%) |
| | 6.84 g | (36.1% w/w) |

Example 12

The compositions of Examples 10 and 12 were used in treating a Diabetic Foot Ulcer (DFU) in a male patient presented with an inverted, roughly triangular shaped DFU. The DFU was ~3 cm across the top, and ~3 cm from top to bottom. The DFU was surrounded within a vertically oriented, somewhat oval shaped callus. The DFU was located on the left foot. The patient has had type 1 diabetes for 55 years, and has neuropathy and some ischemia in both feet. The patient has controlled the diabetes well in recent years, having A1c's ranging from 5.9-6.5 for the last several years. However, this patient did not have such good control of the diabetes for many of the preceding years, and often had A1c's higher than 11. The patient is currently on an insulin pump, and a continuous glucose sensor. This combination enables the patient to practice rigorous blood glucose control, with much less risk of hypoglycemia and hyperglycemia than without this combination of apparatuses.

The patient was treated with debridement, offloading, and infection control.

DEBRIDEMENT—The DFU was debrided 14 days following diagnosis. The site immediately began to form a scab that corresponded to the original size/shape of the DFU. This was the expected outcome of the debridement procedure.

OFFLOADING—Soft insoles, with an aperture shaped like the DFU, and ~2-3 mm larger than the DFU were placed in the shoe. Throughout the therapy, two insoles were used to maintain the elevation of the DFU above the shoe sole. This succeeded in reducing most of the pressure on the DFU, and the patient therefore remained ambulatory throughout the therapy.

INFECTION CONTROL—The patient was immediately placed on a 17 day course of antibiotic therapy as follows: SULFAMETHAZOLE/TRIMETHOPRIM 800/160 MG, and APO-AMOXI CLAY 875/125 MG (AMOXICILLIN/CLAVULANIC ACID) twice daily.

In addition to the antibiotic therapy, the DFU was treated two-three times daily with the topically applied droplet formulation of Example 10. This topical, transdermal, targeted composition enables higher, more efficacious concentrations of the active agent(s) to reach the lesion, while systemic concentrations are maintained at trivial levels. This leads to more effective infection control.

The foot was wrapped in gauze at the region of the foot containing the DFU.

The wound dressing was replaced twice daily for the remainder of the therapy. The droplet composition of Example 10 was applied to the DFU each time the dressing was changed. The droplet composition of Example 11 replaced the Example 10 composition after three weeks. Two finger bandages were placed over the DFU each time the dressing was changed. The foot was treated with a moisturizing lotion, AVEENO Daily Moisturizing Lotion, at each dressing change. The foot was then wrapped with gauze each time the dressing was changed. It was noted that the DFU was draining a clear fluid at each dressing exchange.

On day 31, the DFU scab began peeling some shards, and disclosed normal appearing skin beneath the freshly bared locations. The peeling of shards from the DFU continued, and by day 84, the DFU was reduced in size to ~1 cm by ~1 cm, and had a nominally square shape. Also, by day 84, it was noted that the DFU was no longer draining any fluid at each dressing exchange. It was concluded that no infection remained at the site by this time. However, the treatment with the anti-infective composition of Example 10 continued at each dressing change. The anti-infective composition of Example 10 also aids in healing.

On day 97, the final debridement of the scab was accomplished, and the skin under the removed scab was normal appearing, and there were no signs of infection. The patient continues to wear shoes having soft insoles in them, in order to reduce trauma.

I claim:

1. A method of treating the skin of an individual that is suffering from diabetes, wherein the individual has a site of concern on the skin in need of treatment, comprising applying to the site of concern a topical skin treatment composition comprising polyethylene glycol (PEG) 200 or 400, triclosan, a salicylate, bronopol, isopropanol and, optionally, an acrylic emulsion,
wherein the weight percent of the PEG in the composition is 0.001%-40%, and
wherein the composition spreads evenly when coated onto skin.

2. The method of claim 1, wherein the site of concern on the skin in need of treatment comprises a skin ulcer.

3. The method of claim 2, wherein the site of concern on the skin in need of treatment comprises refractory skin infection.

4. The method of claim 1, wherein the site of concern in need of treatment is an insertion point for a medical device, comprising inserting the medical device into the skin of the individual at the insertion point through the topical skin treatment composition, wherein no infection occurs for at least about 5 days following the insertion of the medical device.

5. The method of claim 4, wherein the composition further comprises a solvent and further comprising allowing the solvent to evaporate to produce a skin treatment layer/coating on the skin prior to inserting the medical device.

6. The method of claim 4, wherein the composition is applied prior to insertion of the medical device and is effective to reduce infection at the medical device insertion site for at least about 5 days following the insertion of the medical device and enables a drug burden to remain in an effective range for an extended period.

7. The method of claim 4, wherein the medical device is an insulin pump needle or a continuous glucose monitor.

8. The method of claim 4, wherein the medical device is selected from the group consisting of a needle, an infusion set or device, a peripheral venous catheter or needle, an indwelling infusion needle, a butterfly needle, a subcutaneous access device, an insulin pump needle, a patient controlled analgesia (PCA) pump needle, an arterial catheter, a central venous catheter, a dialysis catheter, a peritoneal dialysis catheter, a nephrostomy catheter, a percutaneous cystostomy catheter, an indwelling paracentesis or pleurocentesis catheter or drain, a percutaneous nephrostomy, a cystostomy tube, a spinal or epidural catheter, and a sensor.

9. The method of claim 1, wherein the weight percent of the PEG in the composition is 0.5%-40%.

10. The method of claim 1, wherein the weight percent of the PEG in the composition is 5%-40%.

11. The method of claim 1, wherein the weight percent of the PEG in the composition is 9%-40%.

12. The method of claim 1, wherein the weight percent of the PEG in the composition is about 30%-40%.

13. The method of claim 1, wherein the weight percent of the PEG in the composition is about 10%-15%.

14. The method of claim 1, wherein the concentration of isopropanol is 10-20%.

15. The method of claim 1, wherein the composition dries in about one to about two minutes at room temperature after application to the skin.

16. The method of claim 4, wherein no infection occurs for at least about 7 days following the insertion of the medical device.

* * * * *